(12) United States Patent
Tan

(10) Patent No.: US 8,293,290 B2
(45) Date of Patent: Oct. 23, 2012

(54) ANNATTO EXTRACT COMPOSITIONS, INCLUDING GERANYL GERANIOLS AND METHODS OF USE

(75) Inventor: Barrie Tan, Amherst, MA (US)

(73) Assignee: American River Nutrition, Inc., Hadley, MA (US)

( * ) Notice: Subject to any disclaimer, the term of this patent is extended or adjusted under 35 U.S.C. 154(b) by 0 days.

(21) Appl. No.: 13/181,692

(22) Filed: Jul. 13, 2011

(65) Prior Publication Data

US 2011/0268719 A1 Nov. 3, 2011

Related U.S. Application Data

(63) Continuation of application No. 11/845,744, filed on Aug. 27, 2007, now Pat. No. 7,989,006, which is a continuation-in-part of application No. 10/821,679, filed on Apr. 8, 2004, now abandoned.

(60) Provisional application No. 60/461,612, filed on Apr. 8, 2003, provisional application No. 60/528,353, filed on Dec. 10, 2003.

(51) Int. Cl.
*A01N 65/00* (2009.01)
(52) U.S. Cl. ..................................................... 424/725
(58) Field of Classification Search ........................ None
See application file for complete search history.

(56) References Cited

U.S. PATENT DOCUMENTS 5,157,132 A * 10/1992 Tan et al. ...................... 549/413

* cited by examiner

*Primary Examiner* — Michael Meller
(74) *Attorney, Agent, or Firm* — Hogan Lovells US LLP

(57) ABSTRACT

Annatto extract composition (AEC), including cis and trans geranyl geraniols (GG) and tocopherol-free C-5 unsubstituted tocotrienols (T3), increases the de novo synthesis of intermediate isoprenoid and distal protein products, including endogenous coenzyme Q10 (CoQ10), dolichols (DL) and all subsequent GG-prenylated and DL-glycosylated proteins, including GG-porphyrinated hemes. This intermediate and distal product replenishment by AEC reverses maladies of myotoxicity (of both drug and non-drug origins), including maladies that affect the muscle, kidney, eye, GI tract and skin, nerve, blood, and CoQ10-related syndromes of energetics and LDL protection. AEC anabolically increases the endogenous de novo CoQ10 synthesis via GG elongation/prenylation of side-chain and conversely CoQ10 catabolically increases the endogenous de novo GG synthesis via beta-oxidation of CoQ10. Also, such AEC decreases de novo synthesis and increases disposal of triglycerides (TG) in humans via PPAR activation and SREBP deactivation. Such drop in TG by AEC reverses maladies of insulin resistance (IR) and metabolic syndrome (MS), prediabetes, diabetes and diabetes-related cardiovascular diseases (CVD). GG activates PPAR and down regulates SREBP transcription factors. This AEC, containing GG, inhibits cancer growth whether or not GG involvement in protein prenylation is required.

8 Claims, 4 Drawing Sheets

ANNATTO EXTRACT COMPOSITIONS, INCLUDING GERANYL GERANIOLS AND METHODS OF USE

RELATED APPLICATIONS

This application is a Continuation of and claims priority upon U.S. application Ser. No. 11/845,744 filed on Aug. 27, 2007 (pending), which is a Continuation-in-Part of U.S. application Ser. No. 10/821,679 filed on Apr. 8, 2004 now abandoned, which is a Non-provisional application of U.S. provisional application Ser. No. 60/461,612 filed on Apr. 8, 2003 and U.S. provisional application Ser. No. 60/528,353 filed on Dec. 10, 2003, the contents of which are all herein incorporated by this reference in their entireties. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

OTHER REFERENCES

Adachi, J. and G. Ioannidis (2000). "Glucocorticoid-induced osteoporosis." Drug Development Research 49: 120-134.

Amin, D., R. Rutledge, et al. (1997). "RPR 107393, a potent squalene synthase inhibitor and orally effective cholesterol-lowering agent: comparison with inhibitors of HMG-CoA reductase." J Pharmacol Exp Ther. 281(2): 746-752.

Ayanian, J., C. Fuchs, et al. (1988). "Lovastatin and rhabdomyolysis." Ann Intern Med. 109: 682-683.

Baker, S. and M. Tarnopolsky (2001). "Statin myopathies: pathophysiologic and clinical perspectives." Clin Invest Med. 24(5): 258-272.

Ballantyne, C., A. Corsini, et al. (2003). "Risk for myopathy with statin therapy in high-risk patients." Arch. Intern. Med. 163(5): 553-564.

Bentinger, M., J. Grunler, et al. (1998). "Phosphorylation of farnesol in rat liver microsomes: properties of farnesol kinase and farnesyl phosphate kinase." Arch Biochem Biophys 353(2): 191-198.

Bi, X., M. Baudry, et al. (2004). "Inhibition of geranylgeranylation mediates the effects of 3-hydroxy-3-methylglutaryl (HMG)-CoA reductase inhibitors on microglia." J. Biol. Chem. 279(46):48238-48245.

Bliznakov, E. (2002). "Lipid-lowering drugs (statins), cholesterol, and coenzyme Q10. The Baycol case—a modern Pandora's box." Biomed Pharmacother. 56(1): 56-59.

Cenedella, R. (1995). "Role of transcription, translation, and protein turnover in controlling the distribution of 3-hydroxy-3-methylglutaryl coenzyme A reductase in the lens." Invest Ophthalmol V is Sci. 36(10): 2133-2141.

Cenedella, R. (1997). "Posttranscriptional regulation of 3-hydroxy-3-methylglutaryl coenzyme A reductase in lens epithelial cells by mevalonate-derived nonsterols." Exp Eye Res. 65(1): 63-72.

Chamberlain, L. (2001). "Inhibition of isoprenoid biosynthesis causes insulin resistance in 3T3-L1 adipocytes." FEBS Letters 507(3): 357-361.

Ciosek, C., D. Magnin, et al. (1993). "Lipophilic 1,1-bisphosphonates are potent squalene synthase inhibitors and orally active cholesterol lowering agents in vivo." J. Biol. Chem 268: 24832-24837.

Colli, S., S. Eligini, et al. (1997). "Vastatins inhibit tissue factor in cultured human macrophages. A novel mechanism of protection against atherothrombosis." Arterioscler Thromb Vasc Biol 17: 265-272.

Craveiro, A. A., et al., (1989). "The Presence of Geranylgeraniol in Bixa Orelana Linn.," Quimica Nova, 12(3):297-298.

Cruz, A. and B. Gruber (2002). "Statins and osteoporosis: Can these lipid-lowering drugs also bolster bones?" Cleveland Clinic Journal of Medicine 69(4): 277-288.

Danesi, R., C. McLellan, et al. (1995). "Specific labeling of isoprenylated proteins: application to study inhibitors of the post-translational farnesylation and geranylgeranylation." Biochem Biophys Res Commun. 206(2): 637-643.

DeFronzo, R. A. (1998). "Pathogenesis of Type 2 Diabetes: Metabolic & Molecular Implications for Identifying Diabetes Genes." Ann. Rev. Diabetes: 1-93.

Flint, O., B. Masters, et al. (1997). "HMG CoA reductase inhibitor-induced myotoxicity: pravastatin and lovastatin inhibit the geranylgeranylation of low-molecular-weight proteins in neonatal rat muscle cell culture." Toxicol Appl Pharmacol. 145(1): 99-110.

Flint, O., B. Masters, et al. (1997). "Inhibition of cholesterol synthesis by squalene synthase inhibitors does not induce myotoxicity in vitro." Toxicol Appl Pharmacol 145(1): 91-98.

Folkers, K., A. Osterborg, et al. (1997). "Activities of vitamin Q10 in animal models and a serious deficiency in patients with cancer." Biochem Biophys Res Commun. 234(2): 296-299.

Gavish, D., E. Leibovitz, et al. (2000). "Bezafibrate and simvastatin combination therapy for diabetic dyslipidaemia: efficacy and safety." J. Intern. Med. 247: 563-569.

Grünler, J., J. Ericsson, et al. (1994). "Branch-point reactions in the biosynthesis of cholesterol, dolichol, ubiquinone and prenylated proteins." Biochim Biophys Acta. 1212(3): 259-77.

Guillet-Deniau, I., et al. (2003). "Glucose induces de novo fatty acid synthesis in rat skeletal muscle through a SREBP-1c dependent pathway." Diabetes 52(Suppl. 1): extended abstract. 1024P.

Hamilton-Craig, I. (2001). "Statin-associated myopathy." Med J Aust. 175(9): 486-489.

Haslinger, B., M. Goedde, et al. (2002). "Simvastatin Increases Fibrinolytic Activity in Human Peritoneal Mesothelial Cells Independent of Cholesterol Lowering." Kidney International 62(5): 1611-1619.

Hevener, A., W. He, et al. (2003). "Muscle-specific Pparg deletion causes insulin resistance." Nat Med. 9(12): 1491-1497.

Holdaas, H., A. Jardine, et al. (2001). "Effect of fluvastatin on acute renal allograft rejection: a randomized multicenter trial." Kidney Int. 60(5): 1990-1997.

Johnson, T. E., X. Zhang, et al. (2004). "Statins induce apoptosis in rat and human myotube cultures by inhibiting protein geranylgeranylation but not ubiquinone." Tox. Appl. Pharma. 200:237-250.

Johnston, S. and L. Kelland (2001). "Farnesyl transferase inhibitors—a novel therapy for breast cancer." Endocr Relat Cancer. 8(3): 227-235.

Jondiko, I. J. O. and Pattenden, G., (1989). "Terpenoids and an Apocarotenoid from Seeds of Bixa Orellana," Phytochemistry, 28(11):3159-3162.

Judy, W., T. Nguyen, et al. (2004). "Evidence for regression of PSA and tumor size in patients with prostate cancer." Submitted for publication in Proc. Natl. Acad. Sci.

Kotti, T. J., D. M. Ramirez et al. (2006). "Brain cholesterol turnover required for geranylgeraniol production and learning in mice." Proc. Natl. Acad. Sci. USA 103(10): 3869-74.

Kraegen, E. (1998). "Physiologic manifestations of PPAR-gamma activation: preclinical studies." Clinical Courier 16(48): 5-7.

Lankin, V., A. Tikhaze, et al. (2000). "Intensification in vivo of free radical oxidation of low density lipoproteins in plasma from patients with myocardial ischemia treated by HMG-CoA-reductase pravastatin and suppression of lipid peroxidation by ubiquinone Q10." Biull Eksp Biol Med. 129(2): 176-179.

Lehmann, J., L. Moore, et al. (1995). "An antidiabetic thiazolidinedione is a high affinity ligand for peroxisome proliferator-activated receptor gamma (PPAR gamma)." J Biol Chem. 270(22): 12953-12956.

Luckman, S., F. Coxon, et al. (1998). "Heterocycle-containing bisphosphonates cause apoptosis and inhibit bone resorption by preventing protein prenylation: evidence from structure-activity relationships in J774 macrophages." J Bone Miner Res. 13(11): 1668-1678.

McCarty, M. (1999). "Can correction of sub-optimal coenzyme Q status improve beta-cell function in type II diabetics?" Med Hypotheses. 52(2): 397-400.

McGuire, T. and S. Sebti (1997). "Geranylgeraniol potentiates lovastatin inhibition of oncogenic H-Ras processing and signaling while preventing cytotoxicity." Oncogene 14: 305-312.

McLaughlin, T., F. Abbasi, et al. (2003). "Prediction of IR with plasma TG or TG/HDL ratio." Diabetes 52(Suppl. 1): A224 extended abstract. 962P.

Miller, P. (2001). "Bisphosphonates for the prevention and treatment of corticosteroid-induced osteoporosis." Osteoporos Int. Suppl 3: S3-S10.

Miguel, K., A. Pradines, et al. (1998). "Competitive Inhibition of Choline Phosphotransferase by Geranylgeraniol and Farnesol Inhibits Phosphatidylcholine Synthesis and Induces Apoptosis in Human Lung Adenocarcinoma A549 Cells." J. of Biol. Chem. 273(40): 26179-26186.

Olbricht, C., C. Wanner, et al. (1997). "Accumulation of lovastatin, but not pravastatin, in the blood of cyclosporine-treated kidney graft patients after multiple doses." Clin Pharmacol Ther. 62(3): 311-321.

Omar, M., J. Wilson, et al. (2001). "Rhabdomyolysis and HMG-CoA reductase inhibitors." The Annals of Pharmacotherapy 35(9): 1096-1107.

Ownby, S. and R. Hohl (2002). "Farnesol and geranylgeraniol: prevention and reversion of lovastatin-induced effects in NIH3T3 cells." Lipids 37(2): 185-92.

Pearce, B., R. Parker, et al. (1992). "Hypocholesterolemic activity of synthetic and natural tocotrienols." J Med Chem. 35(20): 3595-3606.

Peters, J., N. Hennuyer, et al. (1997). "Alterations in lipoprotein metabolism in peroxisome proliferator-activated receptor alpha-deficient mice." J Biol Chem. 272(43): 27307-27312.

Poels, P. and F. Gabreels (1993). "Rhabdomyolysis: a review of the literature." Clin. Neurol. Neurosurg. 95: 175-192.

Polyerino, A. and S. Patterson (1997). "Selective activation of caspases during apoptotic induction in HL-60 cells. Effects Of a tetrapeptide inhibitor." J Biol Chem. 272(11): 7013-7021.

Qureshi, et al., (1995). "Response of Hypercholesterolemic Subjects to Administration of Tocotrienols," Lipids, 30(12).

Raner, G., A. Muir, et al. (2002). "Farnesol as an inhibitor and substrate for rabbit liver microsomal P450 enzymes." Biochem Biophys Res Commun. 293(1): 1-6.

Regazzi, M., I. Iacona, et al. (1993). "Altered disposition of pravastatin following concomitant drug therapy with cyclosporin A in transplant recipients." Transplant Proc. 25: 2732-2734.

Rogers, M. (2000). "Statins: lower lipids and better bones?" Nature Medicine 6(1): 21-23.

Saito, J., J. Davis, et al. (1995). "Users of low-dose glucocorticoids have increased bone loss rates: a longitudinal study." Calcif Tissue Int. 57(2): 115-119.

Schlienger, R., W. Haefeli, et al. (2001). "Risk of cataract in patients treated with statins." Arch Intern Med. 161(16): 2021-2026.

Sever, N., B. Song, et al. (2003). "Insig-dependent ubiquitination and degradation of mammalian 3-hydroxy-3-methylglutaryl-CoA reductase stimulated by sterols and geranylgeraniol." J. Biol. Chem. 278(52):52479-52490.

Smith, P., R. Eydelloth, et al. (1991). "HMG-CoA reductase inhibitor-induced myopathy in the rat: cyclosporine A interaction and mechanism studies." J Pharmacol Exp Ther. 257(3): 1225-1235.

Smith, S. (1998). "The molecular pharmacology of PPAR-gamma." Clinical Courier 16(48): 3-4.

Song, B., R. A. DeBose-Boyd, et al. (2006). "Insig-dependent ubiquitination and degradation of 3-hydroxy-3-methylglutaryl coenzyme A reductase stimulated by delta- and gamma-tocotrienols." J. Biol. Chem. 281(35):25054-25061.

Spach, D., J. Bauwens, et al. (1991). "Rhabdomyolysis associated with lovastatin and erythromycin use." West J. Med. 154: 213-215.

Staels, B., J. Dallongeville, et al. (1998). "Mechanism of action of fibrates on lipid and lipoprotein metabolism." Circulation 98(19): 2088-2093.

Stark, W., M. Blaskovich, et al. (1998). "Inhibiting geranylgeranylation blocks growth and promotes apoptosis in pulmonary vascular smooth muscle cells." Am J Physiol. 275: L55-L63.

Takahashi, N., T. Kawada, et al. (2002). "Dual action of isoprenols from herbal medicines on both PPARgamma and PPARalpha in 3T3-L1 adipocytes and HepG2 hepatocytes." FEBS Lett. 514(2-3): 315-322.

Talley, N., A. Weaver, et al. (1992). "Onset and disappearance of gastrointestinal symptoms and functional gastrointestinal disorder." Am J Epidemiol. 136(2): 165-177.

Thai, L., J. S. Rush, et al. (1999). "Farnesol is utilized for isoprenoid biosynthesis in plant cells via farnesyl pyrophosphate formed by successive monophosphorylation reactions." Proc Natl Acad Sci 96(23): 13080-13085.

Theriault, A., et al., (1999). "Tocotrienol: A Review of Its Therapeutic Potential," Clinical Biochemistry, 32(5):309-319.

Thibault, A., D. Samid, et al. (1996). "Phase I study of lovastatin, an inhibitor of the mevalonate pathway, in patients with cancer." Clin Cancer Res. 2(3): 483-491.

VERIS (1989). The role of Vitamin E in exercise, Vitamin E Research & Information Service (November).

VERIS (1990). Protective role of vitamin E in cataract development, Vitamin E Research & Information Service (February).

Watkins, T. R. and Bierenbaum, M. L., (1999). "Tocotrienols: Biological and Health Effects," in Antioxidant Status, Diet, Nutrition, and Health, Andreas M. Papas, ed. (CRC Press) pp. 479-496.

Watts, G., C. Castelluccio, et al. (1993). "Plasma coenzyme Q (ubiquinone) concentrations in patients treated with simvastatin." J Clin Pathol. 46(11): 1055-1057.

Watts, N., D. Freedholm, et al. (1999). "The clinical tolerability profile of alendronate." Int J Clin Pract Suppl. 101: 51-61.

Willson, T., M. Lambert, et al. (2001). "Peroxisome proliferator-activated receptor gamma and metabolic disease." Annu Rev Biochem. 70: 341-367.

Wong, W., J. Dimitroulakos, et al. (2002). "HMG-CoA Reductase Inhibitors and the Malignant Cell: the Statin Family of Drugs as Triggers of Tumor-Specific Apoptosis." Leukemia 16: 508-519.

Yu, W., et al., (1999). "Induction of Apoptosis in Human Breast Cancer Cells by Tocopherols and Tocotrienols," Nutrition and Cancer, 33(1):26-32.

BACKGROUND OF THE INVENTION

1. Field of the Invention

The invention is on the compositions and uses of the extract from the annatto seed and such extract that is annatto oil or oleoresin containing non-saponifiables, especially non-saponifiable terpenoids.

2. Description of the Related Art

Tocotrienols generally are classified as farsnesylated chromanols (FC) and mixed terpenoids (US 2004-0202740 A1, Tan). Tocopherol and tocotrienol are believed to have beneficial effects because they act as antioxidants. Tocotrienols, in particular, have been documented to possess hypocholesterolemic effects as well as an ability to reduce atherogenic apolipoprotein B and lipoprotein plasma levels. Further, tocotrienols are believed to be useful in the treatment of cardiovascular disease and cancer (Theriault, A., et al., "Tocotrienol: A Review of its Therapeutic Potential," Clinical Biochemistry, 32:309-319 (July 1999); and "Tocotrienols: Biological and Health Effects," in Antioxidant Status, Diet, Nutrition, and Health, Papas, ed. (CRC Press), pp. 479-496 (1999)). Delta-tocotrienol and gamma-tocotrienol, in particular, have been identified as effective suppressants of cholesterol activity (Qureshi, et al., "Response of Hypercholesterolemic Subjects to Administration of Tocotrienols," Lipids, 30(12) (1995)), and in inducing apoptosis of breast cancer cells (Yu, et al., "Induction of Apoptosis in Human Breast Cancer Cells by Tocopherols and Tocotrienols," Nutrition and Cancer, 33(1):26-32 (1999)).

Tocols, which includes tocopherols and tocotrienols, have several sources, including several vegetable oils, such as rice bran, soybean, sesame and palm oils. Tocotrienols have been discovered in the seeds of Bixa orellana Linn, otherwise known as the achiote tree (Jondiko, I. S., et al., "Terpenoids and an Apocarotenoid from Seeds of Bixa Orellana," Phytochemistry, 28(11):3159-3162 (1989)). However, each source of tocotrienols and tocopherols generally contains more than a single tocol homolog. For example, palm oil and rice bran oil generally include both tocotrienols and tocopherols. Further, alpha-tocopherol has been reported to attenuate certain effects of tocotrienols, such as the cholesterol-suppressive activity of gamma-tocotrienol (Qureshi, et al., supra.). In addition, because of their structural similarity, tocotrienols and tocopherols can be difficult to separate.

Geranyl geraniol (GG) includes acyclic diterpene alcohols and geranyl geraniated terpenoids, and occurs naturally in linseed oil and cedrela toona wood and tomato fruit. Geranyl geraniol also has been discovered to exist in the seeds of Bixa orellana (Craveiro, et al., "The Presence of Geranyl geraniol in Bixa Orellana Linn," Quimica Nova, 12(3):297-298 (1989)). Potential uses for geranyl geraniol include synthesis of co-enzyme $Q_{10}$, vitamin K and tocotrienols. It is believed to inhibit esterification of retinol into inactive retinyl esters and, therefore, may be used to improve skin desquamation and epidermal differentiation (U.S. Pat. No. 5,756,109, issued to Burger, et al. on May 26, 1998). Geranyl geraniol has been employed in conjunction with HMG-CoA reductase inhibitors in treatment of elevated blood cholesterol (WO 99/66929 by Scolnick, published Dec. 29, 1999). Geranyl geraniol also is suspected to be useful for treatment of human prostate cancer (U.S. Pat. No. 5,602,184, issued to Myers, et al. on Feb. 11, 1997).

Bixa orellana Linn, otherwise known as the achiote tree, is a member of the Bixaceae family and is native to tropical America. It is grown commercially in other parts of the world, generally within 20° of the equator or more preferably within 15° of the equator. The seeds of Bixa orellana Linn are the source of a reddish-orange colorant, known as annatto, that contains bixin and orelline, both of which are carotenoid pigments. The colorant is used commonly in foods, dyes and polishes. Typically, annatto is extracted from dehusked seeds in an aqueous caustic solution. The colorant is precipitated from aqueous caustic solution by addition of a suitable acid, such as sulfuric acid. The precipitated colorant is removed by filtration. Filtercake of precipitated annatto colorant is dried and milled to form a commercial product. An oily phase generally is separated from an aqueous caustic phase by centrifugation or by settling. Alternatively, the annatto colorant can be extracted from seeds in an organic solvent, such as hexane, acetone, or an alcohol. Miscella containing color and byproduct oil are allowed to cool sufficiently to precipitate the annatto colorant. The precipitate is separated as bottoms from the organic solvent. The oily phase from the caustic or organic extractions following separation of the annatto precipitate generally are discarded as byproducts.

The phrase "annatto extract" is imprecise and is used by other authors to define a wide array of compositions. Typically, these products contain all the parts of the annatto seed or at least contain the bixins that are used for colorants. It is important to distinguish annatto extracts that contain bixins from the disclosed annatto extracts by the applicants that do not contain bixins or are essentially free of bixins.

U.S. Pat. No. 6,350,453 by Tan discloses the method of obtaining the natural annatto extract, the byproduct solution of Bixa orellana seed components. The final product of the method is a composition containing the natural ratio of isomers of the principal components.

The disclosed method in Tan ('453) uses a "a vegetable oil" or "a rice bran oil" (Column 4, Lines 34-42) in one example to "reduce viscosity" (Line 39). This vegetable oil or rice bran oil was a cooking oil (triglyceride (TG)) which contained traces or none of any tocotrienols, tocopherols or geranyl geraniols.

The vegetable oil was used as a lubricant for the distillation of annatto extract as it becomes more viscous with successive distillations (or "passes"). This is shown in Examples 3 & 4 in Tan ('453) with the use of 10% rice bran oil.

Careful Examination of Example 4 in Tan ('453), going over Passes 1 and 2, after rice bran oil was added, then the Pass 2 distillation, tocotrienol was enriched. The vegetable oil was never distilled with the tocotrienol because the rice bran oil served as a lubricant (viscosity reducer) and not an additive or diluent to the tocotrienol. The tocotrienol enrichment (about 15% to 26.3% in Pass 2, Example 4 or about 19.6% to 33.6% in Pass 2, Example 3) shows that the vegetable oil was left behind as residue and did not distill with tocotrienol. The difference in molecular weights of TG and tocotrienol made this processing possible. In Example 3, the rice bran oil ended in residue of Pass 2 (accounting 32% of the total mass).

The byproduct solution of *Bixa orellana* seed components is obtained after removing the bixins to produce "yellow cake" and has greatly reduced levels of bixins. The byproduct solution is then distilled to obtain a 290-390 Dalton MW fraction. The 290-390 Dalton MW fraction is the fraction that contains geranyl geraniol. The disclosed geranyl geraniols in the application are obtained from the 290-390 Dalton MW fraction of the byproduct solution of *Bixa orellana* seed components.

Geranyl geraniols are 290 Daltons in molecular weight and Bixins are 390-425 Daltons in molecular weight. These molecular weights are easy to calculate from the structures of these chemicals. Additionally, their chemical structures show that geranyl geraniols have 1 oxygen groups and bixins have 4 oxygen groups.

Although the molecular weights of bixins (390-425 Daltons) over lap the molecular weights of tocotrienol and tocopherol (350-450 Daltons), their chemical structure [bixins have 4 oxygen groups; tocotrienols and tocopherols have 2 oxygen groups] inhibits bixins (i.e., they are heavier because they contain the 4 large oxygen groups) distillation from the byproduct solution of *Bixa orellana* seed components and remain in the residue material The higher the number of oxygen groups a molecule contains, the less likely it is to distill. Geranyl geraniol has 1 oxygen group, tocotrienols and tocopherols have 2 oxygen groups, bixins have 4 oxygen groups; and triglycerides have 6 oxygen groups (MW 500-1,000 Daltons). Therefore, geranyl geraniol distills before the tocotrienols and tocopherols, and bixins and triglycerides (being the heaviest/densest) remain in the residue.

It has been discovered that byproduct solutions of *Bixa orellana* seed components contain tocotrienols, including delta- and gamma-tocotrienols, and geranyl geraniol. In particular, it has been discovered that tocotrienols and geranyl geraniol are present in the byproduct oily phase of annatto colorant from annatto seeds and, especially, from whole dehusked annatto seeds.

A "byproduct solution of *Bixa orellana* seed components" is defined herein as a solution derived from *Bixa orellana* seed components having a concentration of annatto colorant significantly reduced from that of *Bixa orellana* seeds themselves. Other common terms for byproduct solution used for commercial products include: oil-soluble annatto color or annatto oil. Generally, the concentration of annatto colorant, which is defined as bixins and other carotenoids, chemically modified, altered or esterified, in byproduct solution of *Bixa orellana* seed is less than about two percent, by weight, such as between about 0.05 weight percent and about 2.0 weight percent.

Annatto extract composition (AEC) typically contains cis and trans isomers of geranyl geraniol (GG) and tocopherol-free tocotrienols (T3) that are essentially delta and gamma isomer forms. Geranyl geraniols belong to a class of terpenoid, more specifically, diterpene isoprenoids containing four isoprene units. The GG may be all in the trans isomer form (only one form possible), and/or contain one or more of cis isomer forms, both of the trans and cis forms are endogenous nutrients; however, they are not vitamins in the classical sense. Both cis and trans GG become substrates for many branch-point reactions needed in the syntheses of downstream isoprenoid and distal protein products.

Geranyl geraniol (cis and trans) has a molecular weight of 290 Daltons, which is much smaller than the tocopherols and tocotrienols, and bixins in the annatto seed. Vitamin E, including tocopherols and tocotrienols, are typically 390-430 Daltons in molecular weight or more broadly 350-450 Daltons in molecular weight, which includes tocopherols and tocotrienols without any methylated groups in the lower range and tocopherols and tocotrienols with fully methylated groups in the higher range. [Alpha-Tocopherol=430, Beta-Tocopherol=417, Gamma-Tocopherol=417, Delta-Tocopherol=403, Alpha-Tocotrienol=424, Beta-Tocotrienol=411, Gamma-Tocotrienol=410, and Delta-Tocotrienol=396.]

Many physiologic nutrients of small molecular weight are produced from the mevalonate pathway that generates the "isoprenoid pool" (IP) products. Geraniol (G), farnesol (F), and GG are the examples of IP products containing two, three, and four repeating units of five-carbon isoprenes, respectively. Tocotrienols belong to the class of vitamin E that includes tocopherols. It is known that T3's lower cholesterol and treat hypercholesterolemia (Pearce, Parker et al. 1992; Song, DeBose-Boyd 2006). Unlike GG, T3's are not endogenous nutrients, but are produced by plants and have a condensed farnesol tail in its structure.

Farnesol constitutes the last committed step to cholesterol synthesis, but GG is not required for cholesterol synthesis (Flint, Masters et al. 1997; Flint, Masters et al. 1997). GG constitutes the first uncommitted step to cholesterol synthesis, and therefore, the first committed steps in the synthesis of CoQ10, dolichol (DL), heme porphyrin, and GG-prenylated and DL-glycosylated proteins (Baker and Tarnopolsky 2001). Both cis and trans isomeric GGs are required for endogenous isoprenoid substrates for downstream branch-point products (Grünler, Ericsson et al. 1994). Trans-GG is the precursor to all-trans CoQ10 synthesis, which is involved in mitochondrial respiration. Cis-GG is the precursor to DL, DL-glycosylated proteins, and certain GG-prenylated proteins. Dolichol and GG tend to concentrate in the brain and liver but GG is ubiquitously found in many tissues (Grünler, Ericsson et al. 1994). Proteins produced by DL-glycosylation and GG-prenylation will be directed (e.g., structures of protein fold, targets of where it will be delivered, and anchors of how it will be recognized). Deficiency in GG and/or DL leads to improper localization of proteins, producing nonsense proteins and signals. A major use of GG-prenylated protein is in the muscle tissues, and a major use of DL-glycosylated protein is in the nerve tissues. Synthesized proteins via isoprenoid GG and DL are described.

The HMG CoA reductase (HMGR) catalyzes the rate-limiting steps in the lengthy hepatic cholesterol synthesis. The inhibition of HMGR is the target for statin targetment of hypercholesterolemia. However, statins inhibit mevalonate (e.g., one isoprene) at the onset of the formation of the first isoprene, and therefore inhibits all subsequent IP products, including GG (FIG. 1). It is this depletion and deprivation of GG that can produce secondary, but clinically significant, side effects of DL-starved cranial nerve damage and defects typified by neurological dysfunctions (e.g., taste alteration/loss, lack coordination, facial paresis, memory loss, vertigo, peripheral neuropathy, and peripheral nerve palsy). Geranyl geraniol salvages GG-prenylated proteins in brain cells (Thai, S. Rush et al. 1999). Brain cells utilize free GG (not in the activated GG-diphosphate form: GGPP) to restore the IP pool and incorporate it into the protein biosynthesis system. Thus, GG is physiologically and pharmacologically significant in the central nervous system (CNS) (Kotti, T. J., D. M. Ramirez, et al 2006; Sever, N. B. Song, et al 2003; Bi, X., M. Baudry, et al 2004). For example, when isoprenoid products are depleted by statin and bisphosphonate medication, GG replenishes GG-prenylated and DL-glycosylated proteins. Drug side effects are many and they include GG-deprived induction of myotoxicities (e.g., musculoskeletal disorders, muscle cramps/pain, myalgia, myopathy, rhabdomyolysis, and myonecrosis), exo- and endothelial dysfunctions (e.g., upper GI maladies—esophagitis, gastritis/stomatitis, stomach/duodenal ulcer and lower GI maladies—constipation, dyspepsia, gastric dysmotility, abdominal pain) (Watts, Freedholm et al. 1999). GI tract (i.e., esophageal, gastric, duodenal) lesions include perforations, ulcers, bleeds and hemorrhages, maladies all of which come from GG-deprived protein synthesis of the mucosae. Other GG-deprived dysfunctions include ocular maladies (e.g., cataract/lens opacity, dry eyes, corneal abrasion, ophthalmoplegia), anemia, CoQ10, DL and its associated DL-starved maladies, described above. Again, eye problems such as lens opacity and dry eyes can be traced to the deprivation of GG. These side effects include secondary CoQ10-deprived maladies (e.g., mitochondrial dysfunction, ATP/respiration, LDL protection, tiredness/malaise, fibromyalgia, chronic fatigue syndrome, and congestive heart failure). The schematic outline of this invention for GG-deprived maladies is shown in FIG. 2.

Drug-Induced Myopathies Via GG Inhibition

IP product depletion from treatment with statins is serious side effect, so alternatives to statins are proposed for treatment of hypercholesterolemia. Squalene synthase catalyses the first committed step in cholesterol biosynthesis via two F groups head-to-head (FIG. 1). To avoid such global IP depletion, and particularly GG depletion, squalene synthase inhibitors (SSI) target distal isoprenoid squalene inhibition to treat hypercholesterolemia (Ciosek, Magnin et al. 1993; Amin, Rutledge et al. 1997). A unique advantage of SSI, as opposed to statins, is that they do not deplete IP immediate and distal products, such as GG, CoQ10, and DL. Such new drug targets only underscore the unique role of GG and the serious implication of its depletion. However, widespread successful use of statins, and their ever growing expanded uses, emphasizes the importance of the invention for adjunctive therapy to circumvent isoprenoid depletion in general, and GG depletion in particular (Johnson, T. E., X. Zhang, et al 2004).

Isoprenoid pool deprivation and myopathies are common with widespread use of statin drugs for the treatment of hypercholesterolemia, fibrate drugs for the treatment of hypertriglyceridemia, and bisphosphonate drugs for the treatment of osteoporosis. Such widespread use of statins is now extended further because of other non-cholesterol approved uses, other cardiovascular indications/uses, as well as, other statin-in-tandem combination uses. A clinically meaningful adverse event of GG inhibition is a global loss of protein, with consequent myotoxicity. Therefore, AEC is particularly useful in the adjunctive relief to IP deprivation, such as, but not limited to statin, fibrate, and bisphosphonate users.

Non-Drug-Induced Myopathies Via GG Inhibition

Isoprenoid pool deprivation may also occur in the elderly and those with AIDS-HIV where wasting occurs due to protein deficit (Poels and Gabreels 1993; Hamilton-Craig 2001).

CoQ10

CoQ10 is transported in the vascular system via LDL particles. Statins work to inhibit de novo cholesterol synthesis, which also simultaneously inhibit de novo CoQ10 and DL synthesis (Bliznakov 2002). Statins also work to increase the hepatic LDL receptors, hence reducing LDL particles in vascular circulation. Consequently, patients on statins will see a drop in LDL with a corresponding drop in CoQ10 (Watts, Castelluccio et al. 1993).

GG is the first committed step for numerous downstream distal products, including CoQ10 (FIGS. 1 & 4). The GG molecule (MW=290) containing 4 isoprene units anabolizes to CoQ10 molecule (MW=863) containing 10 isoprene units. Conceptually, a minimum of 2 moles of GG is required to anabolize 1 mole of CoQ10 and conversely 1 mole of CoQ10 is required to catabolize to 2 moles of GG. This is illustrated by way of the molar conversion example as follows: A 100 mg of GG (100/290=0.345 mmole) can anabolize to 150 mg of CoQ10 (0.345/2×863).

Hypercholesterolemia

Statin intensifies in vivo LDL oxidation in patients with myocardial ischemia while CoQ10 supplementation suppresses lipid oxidation (Lankin, Tikhaze et al. 2000). Further, animal cells contain about 10-fold more CoQ10 than vitamin E, and the cell preferentially utilizes CoQ10 as an antioxidant.

This invention shows AEC supplementation prevents statin toxicities, increases CoQ10, and the endogenous CoQ10 preferentially protects the LDL, lowers cholesterol and improves endothelial functions all at the same time. For patients on statins, endogenous CoQ10 levels typically drop about 30-40%. Clinically significant adverse effects occur when CoQ10 levels fall below 0.5 ug/mL. AEC also help diabetics on statins by enhancing CoQ10 status which improves beta-cell function in Type 2 diabetes (McCarty 1999).

It is implicit to current discussions that GG is readily bioavailable to cells and tissues. In addition, GG is not cytotoxic as it does not cause cell rounding, a known cellular indicator of myotoxicity (McGuire and Sebti 1997; Ownby and Hohl 2002). In fact, GG prevents and reverses cell rounding caused by statins and bisphosphonates. However, a similar IP product, farnesol, does not have either of these GG benefits. Therefore, the use of AEC takes advantage of the bioavailability and safety of GG to tissues.

Statin inhibits the insulin-responsive glucose transporter (Glut 4), and that such inhibition of IP biosynthesis cause IR in adipocytes (Chamberlain 2001). Glut 4 is a membrane protein that requires GG-prenylation. Therefore, the use of statins and bisphosphonates would inhibit the GG-prenylated biosynthesis of Glut 4, and thereby causing insulin resistance (IR) in adipocytes.

Cancer

A strategic way to inhibit cancer is to employ a farnesyl transferase inhibitor (FTI), since Ras cancer requires farnesyl-prenylation of its protein for survival. These FTIs are known to have toxic effects to cancer patient including GI toxicity, peripheral neuropathy & nerve conduction abnormality, and fatigue (Johnston and Kelland 2001). Surprisingly, all of these toxic effects may be ascribed to GG deficiency. GI toxicity is due in part to GG-associated prenylation of protein on the GI lining. Neuropathy and nerve defects are often related to DL-depleted glycosylation. Fatigue is often of unknown etiologies, commonly associated with chronic fatigue syndromes. They are ascribed to a deficiency in CoQ10, derived endogenously from the GG substrate.

Statin drugs have also been used in cancer treatment. A typical dosage of statins for cancer is 10 times their requirements for cholesterol reduction (Wong, Dimitroulakos et al. 2002). This can lead to serious myotoxicities including myopathy and rhabdomyolysis. GG is not toxic to untransformed cells or to normal cells (Stark, Blaskovich et al. 1998; Ownby and Hohl 2002; Wong, Dimitroulakos et al. 2002).

Cancer patients often have low blood levels of CoQ10. CoQ10 has been used as treatment in patients with breast and prostate cancers (Folkers, Osterborg et al. 1997; Judy, Nguyen et al. 2004). The prostate specific antigen (PSA) and prostate mass of prostate cancer patients after one year of CoQ10 supplementation decreased 71% and 47%, respectively. However, the mechanism of such effect is not yet known. Prostate cancer patients taking up to 600 mg/day CoQ10 is equivalent to taking 400 mg/day supplement of GG (Judy, Nguyen et al. 2004) according to earlier analysis (see CoQ10 section).

CoQ10 reduces the severity but not the incidence of musculoskeletal toxicities and patient complaints (Thibault, Samid et al. 1996; Wong, Dimitroulakos et al. 2002). Supplementation of mevalonate, a direct precursor to GG but not CoQ10, is shown to ameliorate myopathy, suggesting that the toxic effects are not due to CoQ10 deficiency (Smith, Eydelloth et al. 1991). These studies lend corroborative support to the above claim that CoQ10 catabolizes to GG, at least in parts, which in turn is responsible for partial reversal of myopathy. It may also be understood that it is GG, not CoQ10 per se, reverses myopathy.

While many biological processes are anabolic in nature, catabolic processes are also well known. One such isoprenoid catabolism is the conversion of cholesterol to Vitamin D, steroid hormones, and bile acids (FIG. 2). Such a strategy of cancer treatment is unique, as both CoQ10 and GG are endogenous nutrients, while the majority of cancer drugs are xenobiotic.

There are numerous strategies that disclose the use of GG for cancer treatment, which directly or indirectly involve GG protein prenylation (McGuire and Sebti 1997; Ownby and Hohl 2002). However, its apoptosis mechanism remains largely unknown. Two hypotheses come closest to explaining the mechanism as a "common effector" or a "coordinated regulator" of apoptosis by GG. GG results in a rapid en masse induction of apoptosis via activation of caspase-3 and possibly caspase-2 (Polyerino and Patterson 1997). GG very quickly induces phosphatidyl choline biosynthesis inhibition at the level of choline phosphotransferase, the last step of CDP-choline known as the Kennedy pathway (Miguel, Pradines et al. 1998). Surprisingly, neither of the two apoptosis hypotheses require GG prenylation nor involve protein synthesis for apoptosis. GG appears to be the common denominator and a very potent compound to induce apoptosis en masse. It should be noted that GGPP is not stable and is unlikely to penetrate cell membranes unaided, but the natural isoprenol GG is bioavailable, and taken up by cells through an active transport system, and/or dephosphorylated sequentially by kinases (Danesi, McLellan et al. 1995; Bentinger, Grunler et al. 1998).

Renal Insufficiency

Renal insufficiency affects about 20 million Americans. The continuous irritation of the peritoneum in peritoneal dialysis patients can result in local peritoneal fibrinolytic activities as measured by fibrinolytic enzyme tissue-type plasminogen activator (t-PA) and plasminogen activator inhibitor-1 (PAI-1). Statins increase the t-PA and decrease the PAI-1 and may cause defects in the actin cytoskeleton (Haslinger, Goedde et al. 2002), which may irritate and thin the peritoneal lining. It is noted that the negative effects of statins can be prevented or reversed by the use of GG (Colli, Eligini et al. 1997; Haslinger, Goedde et al. 2002). Since many statins including cerivastatin, pravastatin, lovastatin, and simvastatin are filtered in part through the kidneys and excreted as urine, these drugs can exasperate the problems of renal insufficient patients.

Organ Transplants

Annually there are approximately 2,000 heart and 14,000 kidney transplants performed in the US. Patients with kidney and heart transplants are normally given cyclosporine to suppress the immune response to organ rejection. The most common side effects of cyclosporine are kidney dysfunction and failure, as measured by elevated blood creatinine and uric acid. These side effects may be caused by decreased efficiency in the glomerular filtration rate (GFR), indicating renal insufficiency. Since most graft patients have elevated lipid levels that can lead to coronary artery disease, statins are often prescribed along with cyclosporine. For these patients, the risks of myopathy and/or rhabdomyolysis are substantially higher (ca 15-80%). Despite the dangers of myotoxicities of this combo therapy, their usage is justified based on benefit-to-risk assessment provided that the statin doses are on the lower end, only one statin is allowed, and no fibrates (Ballantyne, Corsini et al. 2003).

Myotoxicities

Myotoxicity includes all forms and stages of muscle damage including, but not limited to, myalgia, myopathy, and rhabdomyolysis. Myopathy is also associated with generalized myalgia and recurrence of fatigue or weakness (creatine kinase level, CK>10 times the normal value). Rhabdomyolysis is characterized by global skeletal muscle fiber breakdown. Organ damage, typically renal insufficiency or acute renal failure, accompanies rhabdomyolysis when CK>100 times the normal value.

Myopathy and rhabdomyolysis may also have non-drug origins. Among the common causes that are not drug-induced are traumas (e.g. surgery), infections (e.g. viral, bacterial, and fungal), exercise exertion, alcohol abuse, and other inherited, environmental, or metabolic causes (Poels and Gabreels 1993; Hamilton-Craig 2001). Therefore, myotoxicity of both drug-induced and non-drug-induced origins are widespread as evidenced by the mild form, myalgia, to intermediate form, myopathy, to severest form, rhabdomyolysis.

There are many known causal mechanisms for drug-induced myopathies including inhibitions of cytochrome 3A4, HMGR, GG, and P-glycoproteins. Statins and bisphosphonates are particularly effective inhibitors of HMGR and GG. These two classes of drugs have remarkably overlapping modes of action. For example, statins, known for its cholesterol reduction via HMGR inhibition, reduce osteoporosis (Rogers 2000; Cruz and Gruber 2002). Conversely, bisphosphonates, known for bone strengthening via GG inhibition, reduce cholesterol (Ciosek, Magnin et al. 1993). Surprisingly, both statins and bisphosphonates inhibit cancer via FT inhibition (Luckman, Coxon et al. 1998; Wong, Dimitroulakos et al. 2002).

Most drugs are extensively biotransformed by the metalloprotein enzyme cytochrome P450 (CYP) system, with the majority of them processed by CYP 3A4, including statins. These processed drugs are removed from the body through biliary and renal excretions in a safe manner. When enzymatic processing by CYP 3A4 is depressed, drug concentration (e.g. statin) becomes elevated in the blood. Such elevation can occur during statin monotherapy or combo-therapy with erythromycin (where blood statin concentration is known to increase by 3-8 folds) (Ayanian, Fuchs et al. 1988; Spach, Bauwens et al. 1991) or with cyclosporine (where blood statin concentration is known to increase by 6-23 folds) (Regazzi, Iacona et al. 1993; Olbricht, Wanner et al. 1997; Holdaas, Jardine et al. 2001). Similar interactions can occur with other drug classes such as warfarin, antifungals/antibiotics, and niacin. The resultant statin elevation in the vascular system can cause serious GG depletion, leading to myopathy and rhabdomyolysis. It is important to note that GG does not inhibit any of the cytochrome P450 enzymes for which CYP3A4 is a part of (Raner, Muir et al. 2002).

Fibrates are effective in lowering triglyceride and hence are particularly useful for prediabetics and Type II diabetics; however, they tend to have a high toxic side effect of myopathy. For prediabetic and diabetic patients, benefits may outweigh the risk in combo therapy with statins to treat mixed lipidemia, common in this patient group. However, the incidence of myopathy may increase by 10-folds in diabetics as compared to the general population when on combo therapy (i.e. myopathy increased from 0.12% to 1.35%) (Gavish, Leibovitz et al. 2000; Omar, Wilson et al. 2001).

Even in monotherapy, fibrates cause myopathy 5.5 times greater than statins, posing an independent risk for myopathy. Fibrates are excreted through the kidneys, which can cause serious problems even in people with mild renal impairment.

Insulin Resistance

Insulin resistance (IR) is associated with increased risk of cardiovascular disease (CVD), Type 2 diabetes mellitus (T2DM), hypertension, polycystic ovarian syndrome (PCOS) and alcohol-unrelated fatty liver disease. However, plasma insulin measurement is not standardized across clinical laboratories, and therefore is an unreliable marker. Therefore, a surrogate marker was developed for insulin resistance, where the IR criteria are TG/HDL≧3.5 and/or TG≧140 mg/dL (McLaughlin, Abbasi et al. 2003).

GG activates mixed PPARs, both PPARγ at the adipocytes and PPARα at the hepatocytes (Takahashi, Kawada et al. 2002). PPARγ activation in adipose tissues decreases IR (Lehmann, Moore et al. 1995; Willson, Lambert et al. 2001) and PPARα activation in the liver lowers blood lipids (Peters, Hennuyer et al. 1997; Staels, Dallongeville et al. 1998). Furthermore, statin down regulates glucose transporter 4 (Glut 4) expression and thereby suppresses the glucose uptake into cells with consequent IR (Chamberlain 2001). Therefore, IP products that are decimated by statin inhibition may inhibit the GG-prenylated protein synthesis of Glut 4.

Peroxisomal Proliferator Activated Receptors

Peroxisomal proliferator activated receptors (PPAR) are members of the nuclear receptor transcription factors. The metabolic consequences of PPARγ activation have been researched mostly on adipose tissue where it is largely expressed (Kraegen 1998; Smith 1998), as well as, on muscle tissue (Hevener, He et al. 2003). The metabolic effects of known PPAR activator thiazolidinediones (TZD) are, a) reduces hyperglycemia and hyperinsulinemia, b) lowers FFA and TG levels, c) enhances IS and lowers IR states, and d) requires insulin for glucose-lowering action. Numerous PPARγ activator functions are similar to PPARα activator functions. This PPARα has been actively researched on liver tissue, especially with regards to lipid use (e.g., uptake and beta-oxidation). Even though the action sites of PPARγ (mainly in adipose) and PPARα (mainly in liver) are different, their activations have many overlapping outcomes. Typically TZD and fibrates affect the activation of PPARγ and PPARα, respectively.

Sterol Regulatory Element Binding Protein-1

Sterol regulatory element binding protein-1 (SREBP-1) is a transcription factor that responds to nutritional status and regulates metabolic gene expression in various organs, including liver, adipose and muscle. It has been shown that insulin and glucose induces de novo fatty acid synthesis leading to a rapid increase in lipogenic flux in skeletal muscle. This lipid accumulation is associated with muscle IR in obesity and T2DM, and is stimulated/mediated via the SREBP-1 expression (Guillet-Deniau 2003). As discussed earlier, IR is tightly associated with increased lipids (McLaughlin, Abbasi et al. 2003) and increased insulin or hyperinsulinemia (HI) (DeFronzo 1998). Additionally, the SREBP-1 expression in part controls FFA/TG synthesis, and PPAR expression in part controls FFA/TG uptake and catabolism (Song, B., R. A. DeBose-Boyd 2006).

Other Aspects of GG Deficiencies and Uses:

The upper GI track (esophagus, stomach, and duodenum) is particularly sensitive to perforations, ulcers, and bleeds. Collective adverse events (AE) include, but not limited to, abdominal pain, dyspepsia, esophageal erosion, esophagitis, reflux esophagitis, and the likes in the duodenum. Repairs to the GI track are done by cellular replication and take approximately 2 weeks in esophagus. Repairs by mucosal migration take approximately 2 days in the duodenum and 2 hours in the stomach. Therefore opportunistic AE is most likely to occur in the esophagus followed by duodenum and least likely in the stomach. Not surprisingly, drug-induced upper GI AE are common, especially in the esophagus. These drugs include emepronium bromide, doxycycline, tetracycline antibiotics, iron supplements, quinidine, non-steroid anti-inflammatory drugs (NSAIDs), alprenolol, captopril, theophylline, zidovudine, and bisphosphonates. Studies show 20-30% of patients develop upper GI AE within the first year of bisphosphonate therapy (Talley, Weaver et al. 1992). The mechanism of upper GI ulcer-related events is due to the GI's inability to prenylate protein needed for cellular replication (a much slower process than mucosal migration) caused by drug-induced depletion of GG and localized esophagitis caused by pills slipping through the esophagus (Watts, Freedholm et al. 1999)

Asymptomatic endoscopic abnormalities (e.g. hemorrhages, erosions, and ulcers) are surprisingly high (15%) in normal post menopausal women (Watts, Freedholm et al. 1999).

Steroids are widely used and the most common among them is prednisone. Corticosteroids are used for many inflammatory diseases including but not limited to arthritis, connective tissue disease, asthma, and in heart transplant patients. These corticosteroids have several side effects including rapid loss of bone mass in the first year of use, as high as 15% of patients develop vertebral fractures (Adachi and Ioannidis 2000), loss of bone mineral density even at very low doses, e.g. prednisone at 5 mg/day (Saito, Davis et al. 1995), and a high rate of steroid-induced osteoporosis, higher than osteoporosis in post menopausal women (Miller 2001). To prevent and reverse corticosteroid-induced osteoporosis, bisphosphonates has become the best drug candidate.

The role of Vitamin E in exercise is well known. Muscle damage can occur during exhaustive exercise, even in highly trained athletes. Furthermore, since the body's Vitamin E consumption increases with the amount of exercise, high amounts of Vitamin E are needed for endurance training and for membrane lipid oxidation protection during strenuous exercise (VERIS 1989).

Statins and bisphosphonates can increase the risk of adverse ocular side effects including cataracts (Schlienger, Haefeli et al. 2001). Statins increase the mRNA and the protein mass of HMGR, which translates to an over expression of cholesterol biosynthesis in intact lens (Cenedella 1995; Cenedella 1997). It is suggested that IP products might prevent lens opaqueness, cataract, and lens cholesterol deposition. Cataract removal remains the most common surgery in the US (more than half million per year). The occurrence of cataracts approaches 50% for those 75 years or older. The protective use of Vitamin E against cataract development is well recognized (VERIS 1990). Vitamin E tocotrienols and tocopherols are both powerful antioxidants. However, only tocotrienols, especially delta- and gamma-tocotrienols have been shown to down regulate the mRNA and reduce the protein mass of HMGR.

DEFINITIONS

Annatto extract—A source of material known as a byproduct solution of *Bixa orellana* seed components, which is obtained as an oily oleoresinous material after the bulk of annatto color, is largely removed from either the aqueous extract or solvent extract of annatto seeds. Further, this byproduct contains a tocotrienol component and a geranyl geraniol component and can be used as a source for the recovery of a tocotrienol component and a geranylgeraniol component. The annatto extract contains ≦2% carotenoids, especially bixins, and mostly (30-40%) as light volatiles of MW<250, geranyl geraniols (20-40%) and tocotrienols (10-20%), and other heavy condensates (5-10%).

Annatto Extract Oil—The oily product from the annatto seed extract containing the tocotrienols and tocopherols, collectively tocochromanols (Vitamin E), which are in the 350-450 Dalton MW fraction of the extract. It is denuded or essentially free of carotenoids (bixins), light volatiles, and heavy condensates. Saponifiable vegetable cooking oils, commonly known as triglycerides, which have a range of molecular weights of 500-1000 Daltons, and are essentially free or free of tocotrienols and tocopherols (typically <0.05% Vitamin E) are not included within this definition.

Appropriate Spectrum of Tocols—Mixtures of annatto tocotrienols with other plant extracts to achieve efficacy of the newly constituted tocols or tocochromanols composition. Annatto tocotrienols satisfy this definition by having the highest amount of C5 unsubstituted tocotrienols and the lowest amount of tocopherols, especially alpha-T1.

Chemotactic Bioactive Materials—Biochemical molecules involved in any oxidative/inflammatory process that leads to loss of arterial vasculature.

Corn Oil—The oily product from the corn extract containing the tocotrienols and tocopherols, collectively tocochromanols (Vitamin E), which are in the 350-450 Dalton MW fraction of the extract. Saponifiable vegetable cooking oils, commonly known as triglycerides, which have a range of molecular weights of 500-1000 Daltons, and are essentially free or free of tocotrienols and tocopherols (typically <0.05% Vitamin E) are not included within this definition.

Cottonseed Oil—The oily product from the cottonseed extract containing the tocotrienols and tocopherols, collectively tocochromanols (Vitamin E), which are in the 350-450 Dalton MW fraction of the extract. Saponifiable vegetable cooking oils, commonly known as triglycerides, which have a range of molecular weights of 500-1000 Daltons, and are essentially free or free of tocotrienols and tocopherols (typically <0.05% Vitamin E) are not included within this definition.

Cranberry Seed Oil—The oily product from the cranberry seed extract containing the tocotrienols and tocopherols, collectively tocochromanols (Vitamin E), which are in the 350-450 Dalton MW fraction of the extract. Saponifiable vegetable cooking oils, commonly known as triglycerides, which have a range of molecular weights of 500-1000 Daltons, and are essentially free or free of tocotrienols and tocopherols (typically <0.05% Vitamin E) are not included within this definition.

Essentially Free of Bixins—A composition that contains less than 0.1% by weight of bixins.

Essentially Free Of Tocotrienols—A composition that contains less than 0.1% by weight of Tocotrienols.

Ingestible—descriptive of a manner to administer compressed tablets, softgel gelatin, hard gel two-piece gelatin, beads, granules, and/or liquid coats.

Litchi Seed Oil—The oily product from the litchi seed extract containing the tocotrienols and tocopherols, collectively tocochromanols (Vitamin E), which are in the 350-450 Dalton MW fraction of the extract. Saponifiable vegetable cooking oils, commonly known as triglycerides, which have a range of molecular weights of 500-1000 Daltons, and are essentially free or free of tocotrienols and tocopherols (typically <0.05% Vitamin E) are not included within this definition.

Medicament—a substance used in therapy.

MW (Molecular Weight) Fraction—Refers to the part (fraction) of a substance (i.e., natural extract) that has chemicals of that molecular weight. A standard analytical tool in Biochemistry or Chemistry is the separation of a substance into its various individual chemicals by their molecular weight. Typical methods include column chromatography, HPLC, and SDS-PAGE. Each of these analytical tools will separate a complex substance (i.e., natural extract) so the individual chemicals will travel at different rates through the medium (e.g., silica or coated/reversed phase silica, sepharose beads or polymerized gels). In the case of column chromatography or HPLC, the carrier solution is collected (e.g., test tubes) as it comes off the column into "fractions". There is a detector on the end of the column which detects the presence of material. The detector charts the "peaks" and the corresponding fraction that contains this material. The molecular weights of these peaks can be calculated using standards with known molecular weights (e.g., Keyhole Limpet Hemocyanin) or the pure compounds with previously identified MWs.

Oat Bran Oil—The oily product from the oat bran extract containing the tocotrienols and tocopherols, collectively tocochromanols (Vitamin E), which are in the 350-450 Dalton MW fraction of the extract. Saponifiable vegetable cooking oils, commonly known as triglycerides, which have a range of molecular weights of 500-1000 Daltons, and are essentially free or free of tocotrienols and tocopherols (typically <0.05% Vitamin E) are not included within this definition.

Olive Oil—The oily product from the olive extract containing the tocotrienols and tocopherols, collectively tocochromanols (Vitamin E), which are in the 350-450 Dalton MW fraction of the extract. Saponifiable vegetable cooking oils, commonly known as triglycerides, which have a range of molecular weights of 500-1000 Daltons, and are essentially free or free of tocotrienols and tocopherols (typically <0.05% Vitamin E) are not included within this definition.

Palm Oil—The oily product from the palm extract containing the tocotrienols and tocopherols, collectively tocochromanols (Vitamin E), which are in the 350-450 Dalton MW fraction of the extract. Saponifiable vegetable cooking oils, commonly known as triglycerides, which have a range of molecular weights of 500-1000 Daltons, and are essentially free or free of tocotrienols and tocopherols (typically <0.05% Vitamin E) are not included within this definition.

Purification of Annatto Extract—A process to obtain isomers of tocotrienol and geranylgeraniol where the ratios are different from found in nature. Purified annatto extract is denuded or essentially free of carotenoids (bixins), light volatiles, and heavy condensates.

Purified Annatto Geranylgeraniol Composition—A composition purified from an annatto extract that contains one or more of the isomers of geranylgeraniol in a ratio that is different from the natural ratio found in an annatto extract. The trans:cis ratio of geranylgeraniols found naturally annatto seeds is within the range of 20:1 to 6:1. However, by using specialized methods, a purified annatto geranylgeraniol composition can be obtained that has altered trans:cis ratios of geranylgeraniols from found in the natural annatto seed. A purified annatto geranylgeraniol composition can have only trans isomer, essentially only trans isomer, and trans:cis ratios from 100:1 to 1:5.

Purified Annatto Tocotrienol Composition—A composition purified from an annatto extract that contains one or more of the isomers of tocotrienol in a ratio that is different from the natural ratio found in an annatto extract.

Rice Bran Oil—The oily product from the rice bran extract containing the tocotrienols and tocopherols, collectively tocochromanols (Vitamin E), which are in the 350-450 Dalton MW fraction of the extract. Saponifiable vegetable cooking oils, commonly known as triglycerides, which have a range of molecular weights of 500-1000 Daltons, and are essentially free or free of tocotrienols and tocopherols (typically <0.05% Vitamin E) are not included within this definition.

Soy Oil—The oily product from the soybean extract containing the tocotrienols and tocopherols, collectively tocochromanols (Vitamin E), which are in the 350-450 Dalton MW fraction of the extract. Saponifiable vegetable cooking oils, commonly known as triglycerides, which have a range of molecular weights of 500-1000 Daltons, and are essentially free or free of tocotrienols and tocopherols (typically <0.05% Vitamin E) are not included within this definition.

Sunflower Seed Oil—The oily product from the sunflower seed extract containing the tocotrienols and tocopherols, collectively tocochromanols (Vitamin E), which are in the 350-450 Dalton MW fraction of the extract. Saponifiable vegetable cooking oils, commonly known as triglycerides, which have a range of molecular weights of 500-1000 Daltons, and are essentially free or free of tocotrienols and tocopherols (typically <0.05% Vitamin E) are not included within this definition.

Tocols—A general term for tocotrienols, tocopherols, mixed tocopherols and tocotrienols, tocotrienol-rich fractions (TRFs) including any additionally separated/fractionated forms, admixtures of annatto tocotrienols and other plant-derived TRFs, appropriate spectrum tocols, admixture of annatto tocotrienols with other tocols in order to standardize the amount and type of tocotrienols and/or tocopherols and the amount or ratio of alpha-tocopherol or other tocopherols present in the admixture.

Tocochromanols—A general term to mean the same as tocols above.

Tocopherol—A chromanol with any degree of substitution with a saturated phytyl tail. Substitution in the chromanol is taken to mean any adduct of the alcohol and/or the ring moiety.

Tocopherol-Free—A preparation having ≧98% tocotrienols and the tocotrienols are predominantly delta-T3 and/or gamma-T3.

Tocotrienol—A chromanol with any degree of substitution with an unsaturated tail of 1 to 3 double bonds. Substitution in the chromanol is taken to mean any adduct of the alcohol and/or the ring moiety.

Wheat Germ Oil—The oily product from the wheat germ extract containing the tocotrienols and tocopherols, collectively tocochromanols (Vitamin E), which are in the 350-450 Dalton MW fraction of the extract. Saponifiable vegetable cooking oils, commonly known as triglycerides, which have a range of molecular weights of 500-1000 Daltons, and are essentially free or free of tocotrienols and tocopherols (typically <0.05% Vitamin E) are not included within this definition.

SUMMARY OF THE INVENTION

The invention relates to a composition comprising annatto extract containing geranyl geraniols and tocotrienols. This composition increases de novo synthesis of subsequent intermediate isoprenoid pool and distal products. The composition has geranyl geraniols in both trans and cis isomers.

The ratio of trans- to cis-isomers in the 290-390 Dalton MW fraction is effected by the conditions (e.g., temperature) during the distillation process. In one embodiment, the trans-to-cis isomer ratio of geranyl geraniols is between 1:100 to 100:1. Preferably, the trans-to-cis isomer ratio of geranyl geraniols is between 1:5 to 5:1. More preferably, the trans-to-cis isomer ratio of geranyl geraniols is >5:1.

In one embodiment, the delta-to-gamma ratio of tocotrienols is between 1:100 to 100:1. Preferably, the delta-to-gamma ratio of tocotrienols is between 1:5 to 5:1. More preferably, the delta-to-gamma ratio of tocotrienols is >5:1.

In one embodiment, the invention is drawn to a method to benefit the health of an animal, comprising administering annatto extract containing geranyl geraniols and increasing an amount of a biological factor to provide or restore a function selected from the group consisting of mitochondrial respiration, lipid protection, heme, DL-glycosylated and GG-prenylated proteins. In a preferred embodiment, the invention is drawn to a method where the biological factor is selected from the group consisting of CoQ10, dolichol (DL), and porphyrin syntheses.

In one embodiment, the invention is drawn to a method of reversing isoprenoid pool deprivation, comprising administering annatto extract containing geranyl geraniols.

In one embodiment, the invention is drawn to a method to increase CoQ10, comprising administering annatto extract containing geranyl geraniols and anabolically increasing the endogenous de novo synthesis of CoQ10.

In one embodiment, the invention is drawn to a method to reverse insulin resistance, comprising administering annatto extract containing geranyl geraniols and potentiating insulin.

In one embodiment, the invention is drawn to a method to reverse insulin resistance, comprising administering annatto extract containing geranyl geraniols and potentiating insulin, further comprising lowering the risk of a disease selected from the group consisting of CVD, T2DM, hypertension, PCOS and fatty liver disease.

In one embodiment, the invention is drawn to a method to activate the nuclear transcription factor PPAR, comprising administering annatto extract containing geranyl geraniols and causing an effect selected from the group consisting of increasing cellular uptake, increasing mitochondrial uptake, increasing beta-oxidation catabolism, increasing triglyceride metabolism, decreasing plasma FFA, decreasing triglycerides, reducing hyperglycemia, reducing hyperinsulinemia, enhancing insulin sensitivity and lowering insulin resistance.

In one embodiment, the invention is drawn to a method to inhibit de novo biosynthesis of fatty acids, comprising administering annatto extract containing geranyl geraniols and deactivating of SREBP-1 expression. In a preferred embodiment, the invention is drawn to a method to inhibit de novo biosynthesis of fatty acids, comprising administering annatto extract containing geranyl geraniols and deactivating of SREBP-1 expression, where the deactivating of SREBP-1 expression causes a decrease in TG.

In an alternative preferred embodiment, the invention is drawn a method to inhibit de novo biosynthesis of fatty acids, comprising administering annatto extract containing geranyl geraniols and deactivating of SREBP-1 expression, where the deactivating of SREBP-1 expression is in organs selected from the group consisting of liver, adipose and skeletal muscle.

In one embodiment, the invention is drawn to a method to inhibit de novo biosynthesis of fatty acids, comprising administering annatto extract containing geranyl geraniols and deactivating of SREBP-1 expression, where there is a decrease in the plasma levels of factors selected from the group consisting FFA, TG, LDL, total cholesterol.

In one embodiment, the invention is drawn to a method to inhibit de novo biosynthesis of fatty acids, comprising administering annatto extract containing geranyl geraniols and deactivating of SREBP-1 expression, where there is a decrease in fat storage.

In one embodiment, the invention is drawn to a method to reduce drug toxicities, comprising administering annatto extract containing geranyl geraniols and reducing the myotoxicities of drugs selected from the group consisting of statins, cyclosporines, fibrates, bisphosphonates, and farnesol transferase inhibitors.

In one embodiment, the invention is drawn to a method to reverse insulin resistance, metabolic syndrome or diabetes, comprising administering annatto extract containing geranyl geraniols, and increasing Glut 4 and decreasing TG.

In one embodiment, the invention is drawn to a composition of annatto extract, which includes geranyl geraniols and tocotrienols, that increases the de novo biosyntheses of all subsequent intermediate isoprenoid pool and distal products.

In one embodiment, the invention is drawn to a composition of annatto extract with geranyl geraniols that has both trans geranyl geraniol and 2-4 cis geranyl geraniols where the trans-to-cis ratio is 1:100 to 100:1. In a preferred embodiment, the invention is drawn to a composition of annatto extract with geranyl geraniols that has both trans geranyl geraniols and 2-4 cis geranyl geraniols where the trans-to-cis ratio is 1:5 to 5:1. In a more preferred embodiment, the invention is drawn to a composition of annatto extract with geranyl geraniols that has both trans geranyl geraniols and 2-4 cis geranyl geraniols where the trans-to-cis ratio is >5:1.

In one embodiment, the invention is drawn to a composition of annatto extract with T3 that has both delta-T3 and gamma-T3, where the delta-to-gamma ratio is 1:100 to 100:1. In preferred embodiment, the invention is drawn to a composition of annatto extract with T3 that has both delta-T3 and gamma-T3, where the delta-to-gamma ratio is 1:5 to 5:1. In a more preferred embodiment, the invention is drawn to a composition of annatto extract with T3 that has both delta-T3 and gamma-T3, where the delta-to-gamma ratio is >5:1.

In one embodiment, the invention is drawn to composition containing geranyl geraniol, especially an unique cis-GG and trans-GG ratio that raises CoQ10, dolichol (DL), and porphyrin syntheses, and thereby provides and/or restores mitochondrial respiration and lipid protection, heme, DL-glycosylated and GG-prenylated proteins, respectively, and described in FIG. 2.

In one embodiment, the invention is drawn to composition of annatto extract containing GG which reverses IP deprivation from drug-induced and non drug-induced maladies. In an alternative embodiment, the invention is drawn to a method of administering an annatto extract containing GG and reversing IP deprivation from drug-induced and non drug-induced maladies.

In one embodiment, the invention is drawn to composition of an annatto extract containing GG that anabolically increases the endogenous de novo synthesis of CoQ10 via GG elongation/prenylation of side chain and conversely CoQ10 catabolically increases the endogenous de novo synthesis of GG via CoQ10 beta-oxidation.

In one embodiment, the invention is drawn to a composition of annatto extract with GG that potentates insulin, which therefore promotes insulin sensitivity, and/or reverses insulin resistance in normal weight and overweight/obese subjects, and in both sexes. In a preferred embodiment, the invention is drawn to a composition of annatto extract with GG that potentates insulin and/or reverses insulin resistance that reduces the risk of CVD, T2DM, hypertension, PCOS and fatty liver disease. In a more preferred embodiment, the invention is drawn to a composition of annatto extract with GG that potentates insulin and/or reverses insulin resistance that activates the nuclear transcription factor PPAR ($\gamma$, $\alpha$, $\delta$, or mixed) expression. In a more preferred embodiment, the invention is drawn to a composition of annatto extract with GG that potentates insulin and/or reverses insulin resistance that activates the nuclear transcription factor PPAR ($\gamma$, $\alpha$, $\delta$, or mixed) expression, and carries out the metabolism-effected increase of cellular and/or mitochondrial uptake and beta-oxidation catabolism. In a more preferred embodiment, the invention is drawn to a composition of annatto extract with GG that potentates insulin and/or reverses insulin resistance that activates the nuclear transcription factor PPAR ($\gamma$, $\alpha$, $\delta$, or mixed) expression, and carries out the metabolism-effected increase of cellular and/or mitochondrial uptake and beta-oxidation catabolism, and then increases triglyceride metabolism. In an even more preferred embodiment, the invention is drawn to a composition of annatto extract with GG that potentates insulin and/or reverses insulin resistance that activates the nuclear transcription factor PPAR ($\gamma$, $\alpha$, $\delta$, or mixed) expression, and carries out the metabolism-effected increase of cellular and/or mitochondrial uptake and beta-oxidation catabolism, and then increases triglyceride metabolism, which then decreases plasma FFA and triglyceride. In an even more preferred embodiment, the invention is drawn to a composition of annatto extract with GG that potentates insulin and/or reverses insulin resistance that activates the nuclear transcription factor PPAR ($\gamma$, $\alpha$, $\delta$, or mixed) expression, and carries out the metabolism-effected increase of cellular and/or mitochondrial uptake and beta-oxidation catabolism, and then increases triglyceride metabolism, which then decreases plasma FFA and triglyceride, and resulting in a reduction of hyperglycemia, HI, enhancement of IS and/or lowering of IR states. In a most preferred embodiment, the invention is drawn to a composition of annatto extract with GG that potentates insulin and/or reverses insulin resistance that activates the nuclear transcription factor PPAR ($\gamma$, $\alpha$, $\delta$, or mixed) expression, and carries out the metabolism-effected increase of cellular and/or mitochondrial uptake and beta-oxidation catabolism, and then increases triglyceride metabolism, which then decreases plasma FFA and triglyceride, and resulting in a reduction of hyperglycemia, HI, enhancement of IS and/or lowering of IR states, where the PPAR ($\gamma$, $\alpha$, $\delta$, or mixed) activation is expressed in numerous organs and tissues in the body.

In one embodiment, the invention is drawn to a composition of annatto extract or annatto extract containing GG that deactivates SREBP-1 expression, and inhibits the de novo biosynthesis of fatty acid. In a preferred embodiment, the invention is drawn to a composition of annatto extract or annatto extract containing GG that deactivates SREBP-1 expression, and inhibits the de novo biosynthesis of fatty acid, and results in a decrease of TG. In another preferred embodiment, the invention is drawn to a composition of annatto extract or annatto extract containing GG that deactivates SREBP-1 expression in various organs, including liver, adipose and skeletal muscle. In a more preferred embodiment, the invention is drawn to a composition of annatto extract or annatto extract containing GG that deactivates SREBP-1 and activates PPAR to control the synthesis and/or metabolism of FFA/TG. In a more preferred embodiment, the invention is drawn to a composition of annatto extract or annatto extract containing GG that deactivates SREBP-1 and activates PPAR to control the synthesis and/or metabolism of FFA/TG, and causes a decrease of lipids in the plasma. In a most preferred embodiment, the invention is drawn to a composition of annatto extract or annatto extract containing GG that deactivates SREBP-1 and activates PPAR to control the synthesis and/or metabolism of FFA/TG, and causes a decrease of lipids in the plasma, and the lipids include LDL and total cholesterol. In the most preferred embodiment, the invention is drawn to a composition of annatto extract or annatto extract containing GG that deactivates SREBP-1 and activates PPAR to control the synthesis and/or metabolism of FFA/TG, and causes a decrease of lipids in the plasma, and the lipids include LDL and total cholesterol, and the animal reduces fat storage and/or loses weight.

In one embodiment, the invention is drawn to a method to reduce drug side effects comprising administering an annatto extract and reducing drug toxicities. In a preferred embodiment, the invention is drawn to a method to reduce drug side effects comprising administering an annatto extract and reducing myotoxicities. In a more preferred embodiment, the invention is drawn to a method to reduce drug side effects comprising administering an annatto extract and reducing myotoxicities, where the myotoxicities are selected from the group consisting of myalgia, myopathy, rhabdomyolysis, and myonecrosis. In a more preferred embodiment, the invention is drawn to a method to reduce drug side effects comprising administering an annatto extract and reducing myotoxicities, where the myotoxicities are selected from the group consisting of myalgia, myopathy, rhabdomyolysis, and myonecrosis, and are caused by drugs selected from the group of statins, cyclosporines, fibrates, farnesyl transferase inhibitor, and bisphosphonates. In a more preferred embodiment, the invention is drawn to a method to reduce drug side effects comprising administering an annatto extract and reducing myotoxicities, where the drug induced toxicities are related to the inhibition of GG, DL, heme, and CoQ10.

In one embodiment, the invention is drawn to a method to reverse insulin resistance, metabolic syndrome and/or diabetes comprising administering an annatto extract or annatto extract containing GG, that reverses and/or salvages Glut 4 inhibition. In a preferred embodiment, the invention is drawn to a method to reverse insulin resistance, metabolic syndrome and/or diabetes comprising administering an annatto extract or annatto extract containing GG, that reverses and/or salvages Glut 4 inhibition, where the levels of Glut 4 increases and/or TG decreases.

In one embodiment, the invention is drawn to a method of correcting nutritional maladies and/or cellular dysmetabolism, comprising administering an annatto extract or annatto extract containing GG, and inhibiting HMGR and/or lowering cholesterol synthesis. In a preferred embodiment, the invention is drawn to a method of correcting nutritional maladies and/or cellular dysmetabolism, comprising administering an annatto extract or annatto extract containing GG, and inhibiting HMGR and/or lowering cholesterol synthesis, and where the inhibiting of HMGR and/or lowering of cholesterol synthesis, does not inhibit endogenous CoQ10 synthesis. In a more preferred embodiment, the invention is drawn to a method of correcting nutritional maladies and/or cellular dysmetabolism, comprising administering an annatto extract or annatto extract containing GG, and inhibiting HMGR and/or lowering cholesterol synthesis, and where the inhibiting of HMGR and/or lowering of cholesterol synthesis, does not inhibit endogenous CoQ10 synthesis and does salvage plasma CoQ10. In a more preferred embodiment, the invention is drawn to a method of correcting nutritional maladies and/or cellular dysmetabolism, comprising administering an annatto extract or annatto extract containing GG, and inhibiting HMGR and/or lowering cholesterol synthesis, and protecting LDL from oxidation and/or increasing cellular ATP energy production. In a most preferred embodiment, the invention is drawn to a method of correcting nutritional maladies and/or cellular dysmetabolism, comprising administering an annatto extract or annatto extract containing GG, and inhibiting HMGR and/or lowering cholesterol synthesis, and decreasing TG, prediabetes and/or diabetes.

In one embodiment, the invention is drawn to a method reducing the effect of maladies comprising the administering of an annatto extract or annatto extract containing GG, wherein GG's distal and intermediate products, and proteins reverse maladies and dysfunctions selected from the group consisting of the central nervous system, GI track, skin (endothelial and exothelial), eye, muscle, blood/heme, and kidney.

In one embodiment, the invention is drawn to a method of inhibiting cancer growth, comprising the administering of an annatto extract or annatto extract containing GG.

In one embodiment, the invention is drawn to a method of supplementation, comprising the administering of an annatto extract or annatto extract containing GG, and preventing statin toxicities, increasing CoQ10, protecting LDL, lowering cholesterol and/or improving endothelial functions.

In one embodiment, the invention is drawn to a method of therapy, comprising the administering of an annatto extract or annatto extract containing GG as a drug adjunct for cancer therapy. In preferred embodiment, the invention is drawn to a method of therapy, comprising the administering of an annatto extract or annatto extract containing GG as a drug adjunct for FTI therapy.

In one embodiment, the invention is drawn to a method of supplementation, comprising the administering of an annatto extract or annatto extract containing GG and reversing myotoxicities.

In one embodiment, the invention is drawn to a method of supplementation, comprising the administering of an annatto extract or annatto extract containing GG in conjunction with CoQ10, and providing ex vivo and in vivo GG substrate or GG alone for treating prostate cancer and/or breast cancer.

In one embodiment, the invention is drawn to a method of supplementation, comprising the administering of an annatto extract or annatto extract containing GG and inhibiting cancer growth where GG involvement is not required in protein prenylation.

In one embodiment, the invention is drawn to a method of supplementation, comprising the administering of an annatto extract or annatto extract containing GG to patients with renal insufficiency and/or kidney dialysis.

In one embodiment, the invention is drawn to a method of supplementation, comprising the administering of an annatto extract or annatto extract containing GG to transplant recipients and reversing and/or minimizing myopathy and rhabdomyolysis, where the supplement is used as an adjunct therapy to calcineurin inhibitors and statins. In a preferred embodiment, the invention is drawn to a method of supplementation, comprising the administering of an annatto extract or annatto extract containing GG to transplant recipients and reversing and/or minimizing myopathy and rhabdomyolysis, where the supplement is used as an adjunct therapy to cyclosporine.

In one embodiment, the invention is drawn to a method of supplementation, comprising the administering of an annatto extract or annatto extract containing GG where drugs deplete GG and reduce protein prenylation, causing myotoxicity.

In one embodiment, the invention is drawn to a method of supplementation, comprising the administering of an annatto extract or annatto extract containing GG, and abrogating the effects of insufficient CYP3A4 processing of statin (in mono- or combo-therapies) and/or reversing the compromise on the vascular system.

In one embodiment, the invention is drawn to a method of supplementation, comprising the administering of an annatto extract or annatto extract containing GG, and using the annatto extract or annatto extract containing GG as an adjunct to mono- and combo-therapies including fibrates. In a preferred embodiment, the invention is drawn to a method of supplementation, comprising the administering of an annatto extract or annatto extract containing GG, and using the annatto extract or annatto extract containing GG as an adjunct to mono- and combo-therapies including fibrates, and with prediabetes, diabetes, and/or hypertriglyceridemia patients.

In one embodiment, the invention is drawn to a method of supplementation, comprising the administering of an annatto extract or annatto extract containing GG, and treating lipidemia of normal or overweight/obese patients. In a preferred embodiment, the invention is drawn to a method of supplementation, comprising the administering of an annatto extract or annatto extract containing GG, and treating lipidemia of normal or overweight/obese patients, and decreasing the level of TG.

In one embodiment, the invention is drawn to a method of supplementation, comprising the administering of an annatto extract or annatto extract containing GG, and activating the nuclear transcription factor PPAR (γ, α, δ or mixed) and carrying out metabolic effects similar to TZDs and fibrates, in various tissues of common sites (adipose, skeletal muscle, and kidney, macrophage, VSMC, endothelial cell) and in various tissues of different sites for PPARγ (heart, gut) and PPARα (liver).

In one embodiment, the invention is drawn to a composition of annatto extract or annatto extract containing GG for a coating to prevent "pill esophagitis", where GG is in a film-coat on compressed tablets, softgel gelatin, hard gel two-piece gelatin, beads, granules, and/or liquid coats.

In one embodiment, the invention is drawn to a method of supplementation, comprising the administering of an annatto extract or annatto extract containing GG, and promoting general upper GI health.

In one embodiment, the invention is drawn to a method of supplementation, comprising the administering of an annatto extract or annatto extract containing GG, and using annatto extract or annatto extract containing GG as an adjunct with combined steroid and bisphosphonate medications.

In one embodiment, the invention is drawn to a composition of annatto extract or annatto extract containing GG, for supplementation during exercise. In a preferred embodiment, the invention is drawn to a composition of annatto extract or annatto extract containing GG for supplementation during heavy training and/or exertion exercise. In a more preferred embodiment, the invention is drawn to a composition of annatto extract or annatto extract containing GG that further contains tocotrienols for supplementation during heavy training and/or exertion exercise.

In one embodiment, the invention is drawn to a method of supplementation, comprising the administering of an annatto extract or annatto extract containing GG, and reducing drug-induced cataract formation. In a preferred embodiment, the invention is drawn to a method of supplementation, comprising the administering of an annatto extract or annatto extract containing GG, and the annatto extract further containing tocotrienols, and reducing drug-induced cataract formation.

In one embodiment, the invention is drawn to a composition of annatto extract or annatto extract containing GG, and the composition further comprising formulation with other synergistic and/or useful non-drug vitamin and mineral nutrients. In a preferred embodiment, the invention is drawn to a composition of annatto extract or annatto extract containing GG, and the composition further comprising formulation with niacin, other B Vitamins, and iron.

In another preferred embodiment, the invention is drawn to a composition of annatto extract or annatto extract containing GG, and the composition further comprising formulation with ubiquinone and/or idebenone.

In another preferred embodiment, the invention is drawn to a composition of annatto extract or annatto extract containing GG, and the composition further comprising formulation with plaunotol and/or micro-protective GI track support nutrients to provide support for the entire "upper-lower" alimentary canal.

In another preferred embodiment, the invention is drawn to a composition of annatto extract or annatto extract containing GG, and the composition further comprising formulation with tocotrienols and tocotrienol rich fractions to promote beneficial effects in the nervous and/or immune system. In a more preferred embodiment, the invention is drawn to a composition of annatto extract or annatto extract containing GG, and the composition further comprising formulation with tocotrienols and tocotrienol rich fractions, where the tocotrienol rich fractions are from palm and rice. In a more preferred embodiment, the invention is drawn to a composition of annatto extract or annatto extract containing GG, and the composition further comprising formulation with tocotrienols and tocotrienol rich fractions to promote beneficial effects in the autonomal nervous system.

In another preferred embodiment, the invention is drawn to a composition of annatto extract or annatto extract containing GG, and the composition further comprising formulation with non-vitamin endogenous nutrients, which include but not limited to, carnitines, CoQ10, alpha lipoic acid, omega 3 fatty acids, linseed/flaxseed oil, creatine, SOD, and NADH.

In another preferred embodiment, the invention is drawn to a composition of annatto extract or annatto extract containing GG, and the composition further comprising formulation with drugs to lessen or eliminate the drug toxicities. In a more preferred embodiment, the invention is drawn to a composition of annatto extract or annatto extract containing GG, and the composition further comprising formulation with drugs to lessen or eliminate the drug toxicities, where the drugs are selected from the group consisting of statins, bisphosphonate, fibrates, cyclosporines, niacin, warfarin/coumadin, antifungals, and antibiotics.

DETAILED DESCRIPTION OF THE INVENTION AND PREFERRED EMBODIMENT

Detailed Description of the Preferred Embodiment

Figure 1:
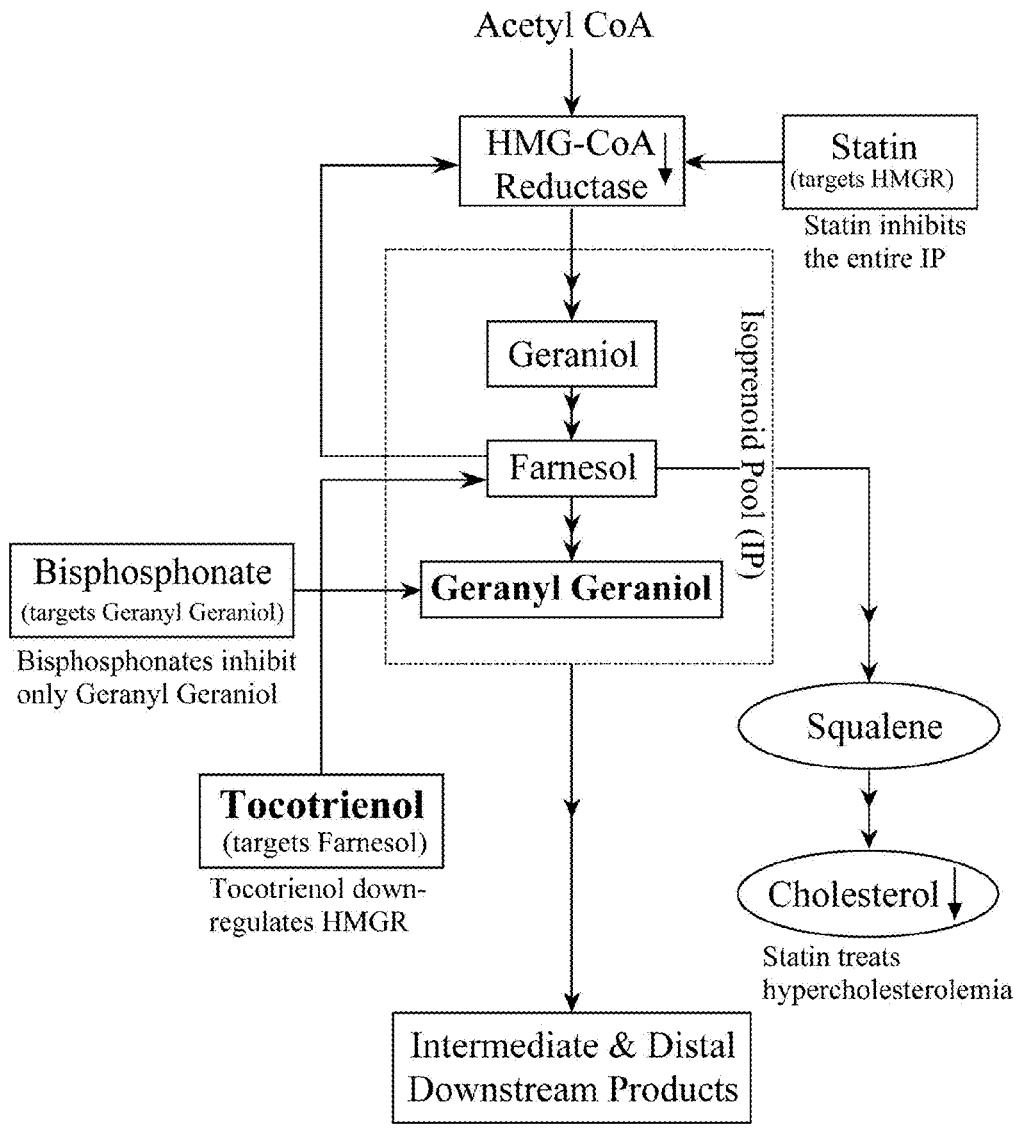
FIG. 1 illustrates the Mevalonate Acid General Pathway.
Figure 2:
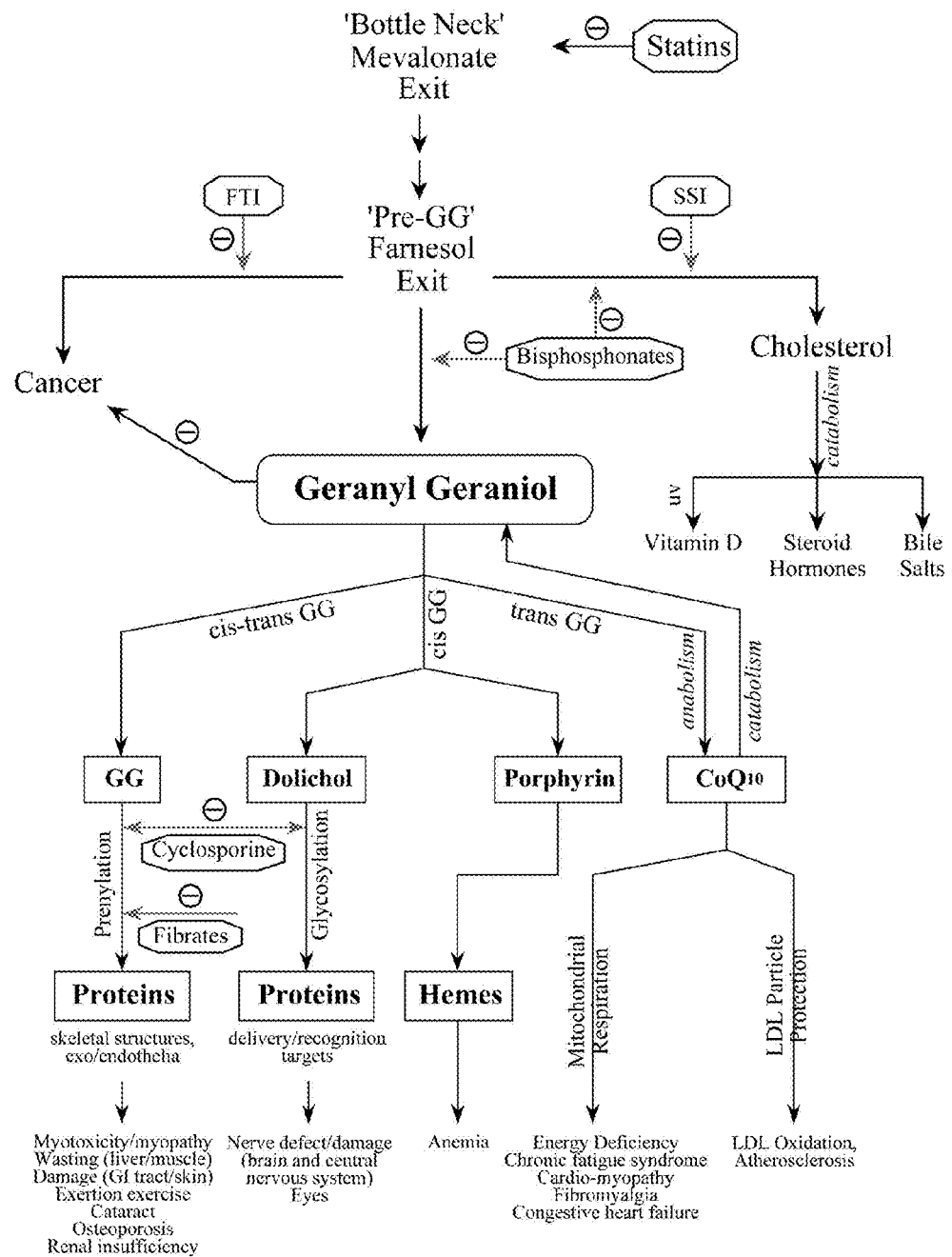
FIG. 2 illustrate the GG downstream distal products and upstream relationships with hatched boxes representing the distal products for GG and octagonal boxes representing the drugs that inhibit specific pathways.

In one embodiment, a composition contains annatto extract. In a preferred embodiment, the composition contains annatto extract with geranyl geraniols. In a more preferred embodiment, the composition contains annatto extract with geranyl geraniols including cis and trans isomer forms. In a more preferred embodiment, the composition contains annatto extract with geranyl geraniols, where the geranyl geraniols are all in the trans isomer form. In a more preferred embodiment, the composition contains annatto extract with geranyl geraniols, where the geranyl geraniols contain one or more of cis isomer forms. In a more preferred embodiment, the composition contains annatto extract with geranyl geraniols, where the geranyl geraniols have a trans-to-cis isomer ratio between 1:100 to 100:1. In a more preferred embodiment, the composition contains annatto extract with geranyl geraniols, where the geranyl geraniols have a trans-to-cis isomer ratio between 1:5 to 5:1. In a more preferred embodiment, the composition contains annatto extract with geranyl geraniols, where the geranyl geraniols have a trans-to-cis isomer ratio 1:1.

In one embodiment, a composition contains annatto extract with tocopherol-free C-5 unsubstituted tocotrienols. In a preferred embodiment, the composition contains annatto extract with tocopherol-free C-5 unsubstituted tocotrienols, where the tocotrienols are essentially in delta and gamma isomer forms. In a preferred embodiment, the composition contains annatto extract with tocopherol-free C-5 unsubstituted tocotrienols, where the tocotrienols extract have a delta-to-gamma ratio between 1:100 to 100:1. In a preferred embodiment, the composition contains annatto extract with tocopherol-free C-5 unsubstituted tocotrienols, where the tocotrienols extract have a delta-to-gamma ratio between 1:5 to 5:1. In a preferred embodiment, the composition contains annatto extract with tocopherol-free C-5 unsubstituted tocotrienols, where the tocotrienols extract have a delta-to-gamma ratio 1:1.

In one embodiment, a composition contains annatto extract with geranyl geraniols and tocopherol-free C-5 unsubstituted tocotrienols. In a more preferred embodiment, the composition contains annatto extract with geranyl geraniols, tocopherol-free C-5 unsubstituted tocotrienols, and inactive and/or active ingredients.

In one embodiment, a composition containing annatto extract increases the de novo synthesis of intermediate isoprenoid. In a preferred embodiment, the composition containing annatto extract increases the de novo synthesis of intermediate isoprenoid and distal protein products. In a more preferred embodiment, the composition containing annatto extract increases the de novo synthesis of endogenous coenzyme Q10 (CoQ10), dolichols (DL) and all subsequent GG-prenylated and DL-glycosylated proteins, including GG-porphyrinated hemes. In a more preferred embodiment, the composition containing annatto extract increases the de novo synthesis of intermediate isoprenoid and distal protein products, and reverses maladies of myotoxicity (both drug and non-drug origins), and maladies that affect the muscle, kidney, eye, GI tract and skin, nerve, blood, and CoQ10-related syndromes of energetics and LDL protection.

In one embodiment, a composition containing annatto extract increases the endogenous de novo CoQ10 synthesis. In a preferred embodiment, the composition containing annatto extract increases the endogenous de novo CoQ10 synthesis, where the de novo CoQ10 synthesis is via GG elongation/prenylation of side-chain. In a more preferred embodiment, the composition containing annatto extract increases the endogenous de novo CoQ10 synthesis, where the de novo CoQ10 synthesis is via GG elongation/prenylation of side-chain, and CoQ10 catabolically increases the endogenous de novo GG synthesis via beta-oxidation of CoQ10.

In one embodiment, a composition containing annatto extract with geranyl geraniols inhibits cancer growth, whether or not GG involvement is required in protein prenylation.

In one embodiment, a composition containing annatto extract with geranyl geraniols decreases de novo synthesis and disposal of triglycerides (TG) in humans.

In one preferred embodiment, a composition containing annatto extract with geranyl geraniols decreases de novo synthesis and disposal of triglycerides (TG) in humans, where the effect is via PPAR activation and SREBP deactivation.

In one embodiment, a composition containing annatto extract with geranyl geraniols causes a decrease in TG and reverses insulin resistance (IR), metabolic syndrome (MS), prediabetes, diabetes and/or diabetes-related cardiovascular diseases (CVD).

In one embodiment, a composition containing annatto extract with geranyl geraniols, where the GG activates PPAR and down regulates SREBP transcription factors.

In one embodiment, a composition containing annatto extract causes endogenous synthesis of CoQ10. In a preferred embodiment, the composition containing annatto extract with geranyl geraniols causes endogenous synthesis of CoQ10. In a more preferred embodiment, the composition containing annatto extract with geranyl geraniols causes endogenous synthesis of CoQ10 in patients taking statin drugs.

In one embodiment, a composition containing annatto extract supplements CoQ10 and causes endogenous synthesis of GG.

In one embodiment, a composition containing annatto extract decreases triglyceride. In a preferred embodiment, a composition containing annatto extract with geranyl geraniols decreases triglyceride. In a more preferred embodiment, the composition containing annatto extract with geranyl geraniols decreases triglyceride, and this decrease is via PPAR activation.

In one embodiment, a composition containing annatto extract with tocotrienols decreases triglyceride. In a more preferred embodiment, the composition containing annatto extract with tocotrienols decreases triglyceride, and the decrease is via PPAR activation.

In one embodiment, a composition containing annatto extract with tocotrienols, where the tocotrienols are tocopherol-free C-5 unsubstituted tocotrienols, decreases triglyceride. In a preferred embodiment, the composition containing annatto extract with tocotrienols, where the tocotrienols are tocopherol-free C-5 unsubstituted tocotrienols, decreases triglyceride, and this decrease is via PPAR activation.

In one embodiment, the composition containing annatto extract decreases insulin resistance.

In one embodiment, a composition containing annatto extract reverses myopathy. In a preferred embodiment, the composition containing annatto extract prevents myopathy. In a more preferred embodiment, the composition containing annatto extract reverses and prevents myopathy.

In one embodiment, a composition containing annatto extract with geranyl geraniols reverses myopathy. In a preferred embodiment, the composition containing annatto extract with geranyl geraniols prevents myopathy. In a more preferred embodiment, the composition containing annatto extract with geranyl geraniols reverses and prevents myopathy.

In one embodiment, a composition containing annatto extract with geranyl geraniols reverses myopathy caused by statins and bisphosphonates. In a preferred embodiment, the composition containing annatto extract with geranyl geraniols prevents myopathy caused by statins and bisphosphonates. In a more preferred embodiment, the composition containing annatto extract with geranyl geraniols reverses and prevents myopathy caused by statins and bisphosphonates.

In one embodiment, a composition containing annatto extract reverses upper GI track damage/erosion. In a preferred embodiment, the composition containing annatto extract prevents upper GI track damage/erosion. In a more preferred embodiment, the composition containing annatto extract reverses and prevents upper GI track damage/erosion.

In one embodiment, a composition containing annatto extract with geranyl geraniols reverses upper GI track damage/erosion. In a preferred embodiment, the composition containing annatto extract with geranyl geraniols prevents upper GI track damage/erosion. In a more preferred embodiment, the composition containing annatto extract with geranyl geraniols reverses and prevents upper GI track damage/erosion.

In one embodiment, a composition containing annatto extract with geranyl geraniols reverses upper GI track damage and/or erosion caused by bisphosphonates. In a preferred embodiment, the composition containing annatto extract with geranyl geraniols prevents upper GI track damage and/or erosion caused by bisphosphonates. In a more preferred embodiment, the composition containing annatto extract with geranyl geraniols reverses and prevents upper GI track damage and/or erosion caused by bisphosphonates.

In one embodiment, a composition containing annatto extract reverses renal insufficiency. In a preferred embodiment, the composition containing annatto extract prevents renal insufficiency. In a more preferred embodiment, the composition containing annatto extract reverses and prevents renal insufficiency.

In one embodiment, a composition containing annatto extract with geranyl geraniols reverses renal insufficiency. In a preferred embodiment, the composition containing annatto extract with geranyl geraniols prevents renal insufficiency. In a more preferred embodiment, the composition containing annatto extract with geranyl geraniols reverses and prevents renal insufficiency.

In one embodiment, a composition containing annatto extract with geranyl geraniols reverses renal insufficiency caused by cyclosporine and/or fibrate drugs. In a preferred embodiment, the composition containing annatto extract with geranyl geraniols prevents renal insufficiency caused by cyclosporine and/or fibrate drugs. In a more preferred embodiment, the composition containing annatto extract with geranyl geraniols reverses and prevents renal insufficiency caused by cyclosporine and/or fibrate drugs.

In one embodiment, a composition containing annatto extract with geranyl geraniols prevents cataract. In a preferred embodiment, the composition containing annatto extract with geranyl geraniols prevents cataract, where the cataracts are caused by statins.

In one embodiment, a composition containing annatto extract with geranyl geraniols protects against protein loss due to cyclosporine and/or fibrate drugs.

In one embodiment, a composition containing annatto extract reverses protein wasting. In a preferred embodiment, the composition containing annatto extract prevents protein wasting. In a more preferred embodiment, the composition containing annatto extract reverses and prevents protein wasting.

In one embodiment, a composition containing annatto extract with geranyl geraniols reverses Protein wasting. In a preferred embodiment, the composition containing annatto extract with geranyl geraniols prevents Protein wasting. In a more preferred embodiment, the composition containing annatto extract with geranyl geraniols reverses and prevents Protein wasting.

In one embodiment, a composition containing annatto extract reverses muscle damage due to exercise. In a preferred embodiment, the composition containing annatto extract prevents damage due to exercise. In a more preferred embodiment, the composition containing annatto extract reverses and prevents damage due to exercise.

In one embodiment, a composition containing annatto extract with geranyl geraniols reverses damage due to exercise. In a preferred embodiment, the composition containing annatto extract with geranyl geraniols prevents damage due to exercise. In a more preferred embodiment, the composition containing annatto extract with geranyl geraniols reverses and prevents damage due to exercise.

In one embodiment, a composition containing annatto extract with geranyl geraniols, where the geranyl geraniols increase the synthesis of CoQ10 and produce the pharmacological and nutraceutical effects of increased CoQ10. In a preferred embodiment, the composition containing annatto extract with geranyl geraniols, where the geranyl geraniols increase the synthesis of CoQ10 and produce pharmacological and/or nutraceutical effects of increased CoQ10, and the pharmacological and/or nutraceutical effects are selected from the group consisting of chronic fatigue syndrome (CFS), cardio-myopathy (CM), energy deficiency, LDL oxidation protection, and atherosclerosis.

In one embodiment, a composition containing annatto extract with geranyl geraniols, where the geranyl geraniols increase the synthesis of dolichol and the increased dolichol levels reverse physical maladies of a dolichol deficit. In a preferred embodiment, the composition containing annatto extract with geranyl geraniols, where the geranyl geraniols increase the synthesis of dolichol and the increased dolichol levels prevent physical maladies of a dolichol deficit. In a more preferred embodiment, the composition containing annatto extract with geranyl geraniols, where the geranyl geraniols increase the synthesis of dolichol and the increased dolichol levels treat physical maladies of a dolichol deficit. In a more preferred embodiment, the composition containing annatto extract with geranyl geraniols, where the geranyl geraniols increase the synthesis of dolichol and the increased dolichol levels reverse, prevent, and/or treat physical maladies of a dolichol deficit.

In one embodiment, a composition containing annatto extract with geranyl geraniols has a beneficial effect on the nervous system. In a preferred embodiment, the composition containing annatto extract with geranyl geraniols has a beneficial effect on the nervous system, where the effect is observed in nerve cells of the central nervous system. In a more preferred embodiment, the composition containing annatto extract with geranyl geraniols has a beneficial effect on the nervous system, where the effect is observed in nerve cells of the central nervous system, and the effect is due to the proper synthesis of protein molecules.

In one embodiment, a composition containing annatto extract with geranyl geraniols mitigates a disease of the nervous system. In a preferred embodiment, the composition containing annatto extract with geranyl geraniols mitigates a disease of the nervous system, where the disease is selected from the group consisting of chronic Alzheimer's, Parkinson's, Familial Dysautonomia.

In one embodiment, a composition containing annatto extract with geranyl geraniols treats a disease of the nervous system. In a preferred embodiment, the composition containing annatto extract with geranyl geraniols treats a disease of the nervous system, where the disease is selected from the group consisting of chronic Alzheimer's, Parkinson's, Familial Dysautonomia.

In one embodiment, a composition containing annatto extract with geranyl geraniols mitigates a disease of muscles. In a preferred embodiment, the composition containing annatto extract with geranyl geraniols mitigates a disease of muscles, where the disease is selected from the group consisting of Muscular Sclerosis, and muscular atrophy.

In one embodiment, a composition containing annatto extract with geranyl geraniols treats a disease of muscles. In a preferred embodiment, the composition containing annatto extract with geranyl geraniols treats a disease of muscles, where the disease is selected from the group consisting of Muscular Sclerosis, and muscular atrophy.

In one embodiment, a composition containing annatto extract with geranyl geraniols, where the geranyl geraniols increase the synthesis of porphyrin. In a preferred embodiment, the composition containing annatto extract with geranyl geraniols and further containing iron, where the geranyl geraniols increase the synthesis of porphyrin. In a more preferred embodiment, the composition containing annatto extract with geranyl geraniols, where the geranyl geraniols increase the synthesis of porphyrin and the increased porphyrin levels reverse physical maladies of a porphyrin deficit. In a more preferred embodiment, the composition containing annatto extract with geranyl geraniols, where the geranyl geraniols increase the synthesis of porphyrin and the increased porphyrin levels reverse physical maladies of a porphyrin deficit and the malady is selected from the group consisting of hemophilia and non-iron induced anemia.

In one embodiment, a composition containing annatto extract with geranyl geraniols, where the geranyl geraniols increase the synthesis of porphyrin and the increased porphyrin levels prevent physical maladies of a porphyrin deficit. In a preferred embodiment, the composition containing annatto extract with geranyl geraniols, where the geranyl geraniols increase the synthesis of porphyrin and the increased porphyrin levels prevent physical maladies of a porphyrin deficit and the malady is selected from the group consisting of hemophilia and non-iron induced anemia.

In one embodiment, a composition containing annatto extract with geranyl geraniols, where the geranyl geraniols increase the synthesis of porphyrin and the increased porphyrin levels reverse, prevent, and treat physical maladies of a porphyrin deficit. In a preferred embodiment, the composition containing annatto extract with geranyl geraniols, where the geranyl geraniols increase the synthesis of porphyrin and the increased porphyrin levels reverse, prevent, and treat physical maladies of a porphyrin deficit and the malady is selected from the group consisting of hemophilia and non-iron induced anemia.

In one embodiment, a composition containing annatto extract with geranyl geraniols, where the geranyl geraniols improve renal insufficiency.

In one embodiment, a composition containing annatto extract with geranyl geraniols, where the geranyl geraniols support the excretory system.

In one embodiment, a composition containing annatto extract with geranyl geraniols, where the geranyl geraniols rebuild the GI track lining.

In one embodiment, a composition containing annatto extract with geranyl geraniols, where the composition is used as an adjunct to reduce toxic effects of drugs.

In one embodiment, a composition containing annatto extract with geranyl geraniols, where the geranyl geraniols of reverse protein deficit. In a preferred embodiment, the composition containing annatto extract with geranyl geraniols, where the geranyl geraniols of reverse protein deficit and the cause of the protein deficient is selected from the group of consisting of trauma, excessive exercise, repetitive exercise, surgery, elderly wasting, and AIDs/HIV.

Additional embodiments are described in the following paragraphs.

Paragraph 1. A composition comprising annatto extract.

Paragraph 2. The composition of Paragraph 1, further comprising geranyl geraniols.

Paragraph 3. The composition of Paragraph 1, further comprising tocotrienols.

Paragraph 4. The composition of Paragraph 2, where the geranyl geraniols include cis and trans isomer forms.

Paragraph 5. The composition of Paragraph 2, where the geranyl geraniols are all in the trans isomer form.

Paragraph 6. The composition of Paragraph 2, where the geranyl geraniols contain one or more cis isomer forms.

Paragraph 7. The composition of Paragraph 2, where the geranyl geraniols have a trans-to-cis isomer ratio between 1:100 to 100:1.

Paragraph 8. The composition of Paragraph 3, where the tocotrienols are essentially in delta and gamma isomer forms.

Paragraph 9. The composition of Paragraph 8, where the tocotrienols have a delta-to-gamma isomer ratio between 1:100 to 100:1.

Paragraph 10. The composition of Paragraph 1, the annatto extract treats maladies selected from the group consisting of drug myotoxicity, non-drug myotoxicity, anemia, CoQ10-related syndrome of energetics and CoQ10-related syndrome of LDL protection.

Paragraph 11. The composition of Paragraph 2, where the geranyl geraniols activate a PPAR.

Paragraph 12. The composition of Paragraph 2, where the geranyl geraniols further down regulate SREBP transcription factors.

Paragraph 13. The composition of Paragraph 1, where the annatto extract increases synthesis of CoQ10.

Paragraph 14. The composition of Paragraph 2, where the geranyl geraniols increases synthesis of CoQ10.

Paragraph 15. The composition of Paragraph 1, further comprising CoQ10, where the CoQ10 increases the synthesis of geranyl geraniols.

Paragraph 16. The composition of Paragraph 1, where the annatto extract decreases triglyceride.

Paragraph 17. The composition of Paragraph 2, where the geranyl geraniols decrease triglyceride.

Paragraph 18. The composition of Paragraph 16, where the decrease in the blood level of the triglyceride has an effect selected from the group consisting of reversal of insulin resistance, metabolic syndrome, prediabetes, diabetes and diabetes-related cardiovascular disease.

Paragraph 19. The composition of Paragraph 2, where the geranyl geraniols protect against protein loss due to a drug selected from the group consisting of cyclosporine, fibrate, statin, and bisphosphonate.

Paragraph 20. The composition of Paragraph 2, where the composition is used as an adjunct to reduce toxic effects of drugs.

Paragraph 21. The composition of Paragraph 1, where the annatto extract treats a malady effecting, selected from the group consisting of, insulin resistance, myopathy, GI track, renal insufficiency, organ transplant, an eye, protein wasting, an exercise injury, central nervous system, muscular system, excretory system, skin, protein deficit, blood, and a cancer.

Paragraph 22. The composition of Paragraph 2, where the geranyl geraniols treat a malady effecting, selected from the group consisting of, insulin resistance, myopathy, GI track, renal insufficiency, organ transplant, an eye, protein wasting, an exercise injury, central nervous system, muscular system, excretory system, skin, protein deficit, blood, and a cancer.

Paragraph 23. The composition of Paragraph 1, where the annatto extract increases synthesis of a biochemical factor selected from the group consisting of CoQ10, dolichol, GG-prenylated protein, DL-glycosylated protein, GG-porphyrinated heme, intermediate isoprenoid, distal protein product, and porphyrin.

Paragraph 24. The composition of Paragraph 2, where the geranyl geraniols increases synthesis of a biochemical factor selected from the group consisting of CoQ10, dolichol, GG-prenylated protein, DL-glycosylated protein, GG-porphyrinated heme, intermediate isoprenoid, distal protein product, and porphyrin.

Paragraph 25. A method to reverse insulin resistance, comprising administering annatto extract containing geranyl geraniols and potentiating insulin.

Paragraph 26. The method of Paragraph 25, further comprising lowering the risk of a disease selected from the group consisting of CVD, T2DM, hypertension, PCOS and fatty liver disease.

Paragraph 27. A method to promote GI tract health, comprising geranyl geraniols and an ingredient selected from the group of consisting of a lower GI nutrient, endogenous nutrient, and non-drug vitamin.

Paragraph 28. A method to prevent pill esophagitis, comprising geranyl geraniols as an excipient in an excipient mix in a pill, selected from the group of consisting of compressed tablet, softgel gelatin, hard gel two-piece gelatin, bead, and granule.

Paragraph 29. A method to reduce drug toxicities, comprising administering annatto extract containing geranyl geraniols and reducing the myotoxicities of a drug selected from the group consisting of statin, cyclosporine, fibrate, and bisphosphonate.

Paragraph 30. A medicament comprising, an ingestible composition with a geranyl geraniol.

Paragraph 31. The medicament of Paragraph 30, wherein the geranyl geraniol is from an extract of annatto.

Paragraph 32. The medicament of Paragraph 30, wherein the geranyl geraniol is in both trans and cis isomer forms.

Paragraph 33. The medicament of Paragraph 32, where the geranyl geraniol is in the trans isomer form.

Paragraph 34. The medicament of Paragraph 32, where the geranyl geraniol is one or more cis isomer forms.

Paragraph 35. The medicament of Paragraph 32, where the geranyl geraniol has a trans-to-cis isomer ratio between 1:100 to 100:1.

Paragraph 36. The medicament of Paragraph 35, where the geranyl geraniols have a trans-to-cis isomer ratio between 1:5 to 5:1.

Paragraph 37. The medicament of Paragraph 35, where the geranyl geraniols have a trans-to-cis isomer ratio is 1:1.

Paragraph 38. The medicament of Paragraph 30, further comprising tocotrienols.

Paragraph 39. The medicament of Paragraph 38, where the tocotrienols are essentially in delta and gamma isomer forms.

Paragraph 40. The medicament of Paragraph 39, where the tocotrienols have a delta-to-gamma isomer ratio between 1:100 to 100:1.

Paragraph 41. The medicament of Paragraph 40, where the tocotrienols have a delta-to-gamma isomer ratio between 1:5 to 5:1.

Paragraph 42. The medicament of Paragraph 40, where the tocotrienols have a delta-to-gamma isomer ratio is 1:1.

Paragraph 43. A method to produce a beneficial effect comprising administering the medicament of Paragraph 30 to a mammal in need of a beneficial effect.

Paragraph 44. A method to produce a beneficial effect comprising administering the medicament of Paragraph 38 to a mammal in need of a beneficial effect.

Paragraph 45. The medicament of Paragraph 30, wherein concentration of the geranyl geraniol in the ingestible composition is greater than 3%.

Paragraph 46. The medicament of Paragraph 45, wherein concentration of the geranyl geraniol in the ingestible composition is greater than 5%.

Paragraph 47. The method of Paragraph 43, where the beneficial effect is treatment of at least one malady selected from the group consisting of drug myotoxicity, non-drug myotoxicity, anemia, CoQ10-related syndrome of energetics and CoQ10-related syndrome of LDL protection.

Paragraph 48. The method of Paragraph 43, where the beneficial effect activates a PPAR.

Paragraph 49. The method of Paragraph 43, where the beneficial effect down regulates SREBP transcription factors.

Paragraph 50. The method of Paragraph 43, where the beneficial effect increases synthesis of CoQ10.

Paragraph 51. The method of Paragraph 43, where the beneficial effect increases synthesis of CoQ10.

Paragraph 52. The medicament of Paragraph 33, further comprising CoQ10.

Paragraph 53. The method of Paragraph 43, where the beneficial effect decreases triglyceride.

Paragraph 54. The method of Paragraph 43, where the beneficial effect decreases triglyceride.

Paragraph 55. The method of Paragraph 53, where the beneficial effect of the decrease in blood level of the triglyceride has an effect selected from the group consisting of reversal of insulin resistance, metabolic syndrome, prediabetes, diabetes and diabetes-related cardiovascular disease.

Paragraph 56. The method of Paragraph 43, where the beneficial effect protects against protein loss due to a drug selected from the group consisting of cyclosporine, fibrate, statin, and bisphosphonate.

Paragraph 57. The method of Paragraph 43, where the beneficial effect is an adjunct to reduce toxic effects of drugs.

Paragraph 58. The method of Paragraph 43, where the beneficial effect treats a malady effecting, selected from the group consisting of, insulin resistance, myopathy, GI track, renal insufficiency, organ transplant, an eye, protein wasting, an exercise injury, central nervous system, muscular system, excretory system, skin, protein deficit, blood, and a cancer.

Paragraph 59. The method of Paragraph 43, where the beneficial effect treats a malady effecting, selected from the group consisting of, insulin resistance, myopathy, GI track, renal insufficiency, organ transplant, an eye, protein wasting, an exercise injury, central nervous system, muscular system, excretory system, skin, protein deficit, blood, and a cancer.

Paragraph 60. The method of Paragraph 43, where the beneficial effect increases synthesis of a biochemical factor selected from the group consisting of CoQ10, dolichol, geranyl geraniol-prenylated protein, DL-glycosylated protein, geranyl geraniol-porphyrinated heme, intermediate isoprenoid, distal protein product, and porphyrin.

Paragraph 61. The method of Paragraph 43, where the beneficial effect increases synthesis of a biochemical factor selected from the group consisting of CoQ10, dolichol, geranyl geraniol-prenylated protein, DL-glycosylated protein, geranyl geraniol-porphyrinated heme, intermediate isoprenoid, distal protein product, and porphyrin.

Paragraph 62. A method to reverse insulin resistance, comprising administering the medicament of Paragraph 30 and potentiating insulin.

Paragraph 63. The method of Paragraph 62, further comprising a beneficial effect of lowering the risk of a disease selected from the group consisting of CVD, T2DM, hypertension, PCOS and fatty liver disease.

Paragraph 64. A method to promote GI tract health, comprising administering the medicament of Paragraph 30 and at least one ingredient selected from the group consisting of a lower GI nutrient, endogenous nutrient, and non-drug vitamin.

Paragraph 65. A method to prevent pill esophagitis, comprising administering the medicament of Paragraph 30 as an excipient in an excipient mix in a pill, selected from the group consisting of compressed tablet, softgel gelatin, hard gel two-piece gelatin, bead, and granule.

Paragraph 66. A method to reduce drug toxicities, comprising administering the medicament of Paragraph 30 and reducing the myotoxicities of a drug selected from the group consisting of statin, cyclosporine, fibrate, and bisphosphonate.

Paragraph 67. A medicament comprising, an ingestible annatto extract composition from a byproduct solution of *Bixa orellana* seed components, wherein the annatto extract composition has purified geranyl geraniol essentially free of tocotrienols.

Paragraph 68. The medicament of Paragraph 67, wherein the geranyl geraniol is in both trans and cis isomer forms.

Paragraph 69. The medicament of Paragraph 68, where the geranyl geraniol is in the trans isomer form.

Paragraph 70. The medicament of Paragraph 68, where the geranyl geraniol is one or more cis isomer forms.

Paragraph 71. The medicament of Paragraph 68, where the geranyl geraniol has a trans-to-cis isomer ratio between 1:100 to 100:1.

Paragraph 72. The medicament of Paragraph 71, where the geranyl geraniols have a trans-to-cis isomer ratio between 1:5 to 5:1.

Paragraph 73. The medicament of Paragraph 71, where the geranyl geraniols have a trans-to-cis isomer ratio is 1:1.

Paragraph 74. A method to produce a beneficial effect comprising administering the medicament of Paragraph 67 to a mammal in need of a beneficial effect.

Paragraph 75. The method of Paragraph 74, where the beneficial effect is treatment of at least one malady selected from the group consisting of drug myotoxicity, non-drug myotoxicity, anemia, CoQ10-related syndrome of energetics and CoQ10-related syndrome of LDL protection.

Paragraph 76. The method of Paragraph 74, where the beneficial effect activates a PPAR.

Paragraph 77. The method of Paragraph 74, where the beneficial effect down regulates SREBP transcription factors.

Paragraph 78. The method of Paragraph 74, where the beneficial effect increases synthesis of CoQ10.

Paragraph 79. The medicament of Paragraph 69, further comprising CoQ10.

Paragraph 80. The method of Paragraph 74, where the beneficial effect decreases triglyceride.

Paragraph 81. The method of Paragraph 74, where the beneficial effect protects against protein loss due to a drug selected from the group consisting of cyclosporine, fibrate, statin, and bisphosphonate.

Paragraph 82. The method of Paragraph 74, where the beneficial effect is an adjunct to reduce toxic effects of drugs.

Paragraph 83. The method of Paragraph 74, where the beneficial effect treats a malady effecting, selected from the group consisting of, insulin resistance, myopathy, GI track, renal insufficiency, organ transplant, an eye, protein wasting, an exercise injury, central nervous system, muscular system, excretory system, skin, protein deficit, blood, and a cancer.

Paragraph 84. The method of Paragraph 74, where the beneficial effect increases synthesis of a biochemical factor selected from the group consisting of CoQ10, dolichol, geranyl geraniol-prenylated protein, DL-glycosylated protein, geranyl geraniol-porphyrinated heme, intermediate isoprenoid, distal protein product, and porphyrin.

Paragraph 85. A method to reverse insulin resistance, comprising administering the medicament of Paragraph 67 and potentiating insulin.

Paragraph 86. The method of Paragraph 85, further comprising a beneficial effect of lowering the risk of a disease selected from the group consisting of CVD, T2DM, hypertension, PCOS and fatty liver disease.

Paragraph 87. A method to promote GI tract health, comprising administering the medicament of Paragraph 67 and at least one ingredient selected from the group consisting of a lower GI nutrient, endogenous nutrient, and non-drug vitamin.

Paragraph 88. A method to prevent pill esophagitis, comprising administering the medicament of Paragraph 67 as an excipient in an excipient mix in a pill, selected from the group consisting of compressed tablet, softgel gelatin, hard gel two-piece gelatin, bead, and granule.

Paragraph 89. A method to reduce drug toxicities, comprising administering the medicament of Paragraph 67 and reducing the myotoxicities of a drug selected from the group consisting of statin, cyclosporine, fibrate, and bisphosphonate.

Paragraph 90. The medicament of Paragraph 67, wherein concentration of the geranyl geraniol in the ingestible composition is greater than 3%.

Paragraph 91. The medicament of Paragraph 90, wherein concentration of the geranyl geraniol in the ingestible composition is greater than 5%.

Paragraph 92. A medicament comprising, a composition of a 290-390 Dalton MW fraction from an extract of a byproduct solution of *Bixa orellana* seed components, wherein the composition contains geranyl geraniols with a trans-to-cis isomer ratio between 1:100 to 100:1.

Paragraph 93. The medicament of Paragraph 92, where the geranyl geraniols is all in the trans isomer form.

Paragraph 94. The medicament of Paragraph 92, where the geranyl geraniols is all one or more cis isomer forms.

Paragraph 95. The medicament of Paragraph 92, where the geranyl geraniols have a trans-to-cis isomer ratio between 1:5 to 5:1.

Paragraph 96. The medicament of Paragraph 33, where the geranyl geraniols have a trans-to-cis isomer ratio is 1:1.

Paragraph 97. A method to produce a beneficial effect comprising administering the medicament of Paragraph 92 to a mammal in need of a beneficial effect.

Paragraph 98. The method of Paragraph 97, where the beneficial effect is treatment of at least one malady selected from the group consisting of drug myotoxicity, non-drug myotoxicity, anemia, CoQ10-related syndrome of energetics and CoQ10-related syndrome of LDL protection.

Paragraph 99. The method of Paragraph 97, where the beneficial effect activates a PPAR.

Paragraph 100. The method of Paragraph 97, where the beneficial effect down regulates SREBP transcription factors.

Paragraph 101. The method of Paragraph 97, where the beneficial effect increases synthesis of CoQ10.

Paragraph 102. The medicament of Paragraph 92, further comprising CoQ10.

Paragraph 103. The method of Paragraph 97, where the beneficial effect decreases triglyceride.

Paragraph 104. The method of Paragraph 97, where the beneficial effect protects against protein loss due to a drug selected from the group consisting of cyclosporine, fibrate, statin, and bisphosphonate.

Paragraph 105. The method of Paragraph 97, where the beneficial effect is an adjunct to reduce toxic effects of drugs.

Paragraph 106. The method of Paragraph 97, where the beneficial effect treats a malady effecting, selected from the group consisting of, insulin resistance, myopathy, GI track, renal insufficiency, organ transplant, an eye, protein wasting, an exercise injury, central nervous system, muscular system, excretory system, skin, protein deficit, blood, and a cancer.

Paragraph 107. The method of Paragraph 97, where the beneficial effect increases synthesis of a biochemical factor selected from the group consisting of CoQ10, dolichol, geranyl geraniol-prenylated protein, DL-glycosylated protein, geranyl geraniol-porphyrinated heme, intermediate isoprenoid, distal protein product, and porphyrin.

Paragraph 108. A method to reverse insulin resistance, comprising administering the medicament of Paragraph 92 and potentiating insulin.

Paragraph 109. The method of Paragraph 108, further comprising a beneficial effect of lowering the risk of a disease selected from the group consisting of CVD, T2DM, hypertension, PCOS and fatty liver disease.

Paragraph 110. A method to promote GI tract health, comprising administering the medicament of Paragraph 92 and at least one ingredient selected from the group consisting of a lower GI nutrient, endogenous nutrient, and non-drug vitamin.

Paragraph 111. A method to prevent pill esophagitis, comprising administering the medicament of Paragraph 92 as an excipient in an excipient mix in a pill, selected from the group consisting of compressed tablet, softgel gelatin, hard gel two-piece gelatin, bead, and granule.

Paragraph 112. A method to reduce drug toxicities, comprising administering the medicament of Paragraph 92 and reducing the myotoxicities of a drug selected from the group consisting of statin, cyclosporine, fibrate, and bisphosphonate.

Other Embodiments

It is to be understood that while the invention has been described in conjunction with the detailed description thereof, the foregoing description is intended to illustrate and not limit the scope of the invention, which is defined by the scope of the appended claims. For example, although the above description relates to human cells, various aspects of the invention might also be applied to cells from other animals (e.g., mammals, avians, fish, crustaceans, domestic and farm animals) by making appropriate modifications to the described methods. Other aspects, advantages, and modifications are within the scope of the following claims.

EXAMPLES

The following examples describe embodiments of the invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the example.

Example 1

Drug and Non-Drug Induced Myopathies Via GG Inhibition

In general, any process that depletes the IP, and in particular the administration of GG is the subject of this AEC invention.

The administration of AEC and GG reverses the effect of GG depletion by drug and non-drug induced myopathies. Also, the administration of GG and AEC containing GG during exercise, particularly in heavy training and exertion exercise reverses the effects of myopathies in animals. An unique application of AEC containing GG is to mix it with tocotrienols, including AEC containing tocotrienols, for heavy training and exertion exercise. There are simultaneous benefits of muscle/protein repair by GG and muscle/oxidation protection by tocotrienols.

Example 2

CoQ10

An average of 20% increase (1.01 to 1.20 µg/mL) in plasma CoQ10 was observed in patients taking AEC containing 20 mg of GG per day. This is equivalent to an exogenous CoQ10 supplementation of 20 mg per day to those knowledgeable in the art. In another investigation involving a single patient, the subject's endogenous CoQ10 rose by 70% from a plasma baseline level of 0.86 µg/mL to 1.47 µg/mL after 3 months of supplementation of AEC containing 27 mg of GG per day. This was the equivalent to an exogenous CoQ10 supplementation of about 35-70 mg/day to those knowledgeable in the art. After the AEC supplementation, the patient experienced increased energy and no longer suffered from chronic fatigue. This outcome was due to the utility of GG in the de novo biosynthesis of endogenous CoQ10.

TABLE 1

Effect of annatto extract supplementation on plasma CoQ10

| Subject | Plasma CoQ10 (μg/ml) | | |
|---|---|---|---|
| | Control | After | Change (%) |
| 1 | 1.03 | 1.21 | 17.5 |
| 2 | 1.09 | 1.34 | 22.9 |
| 3 | 0.97 | 1.06 | 9.3 |
| 4 | 1.12 | 1.35 | 20.5 |
| 5 | 0.86 | 1.06 | 23.3 |
| Mean | 1.02 | 1.20 | 18.8 |

Figure 3:
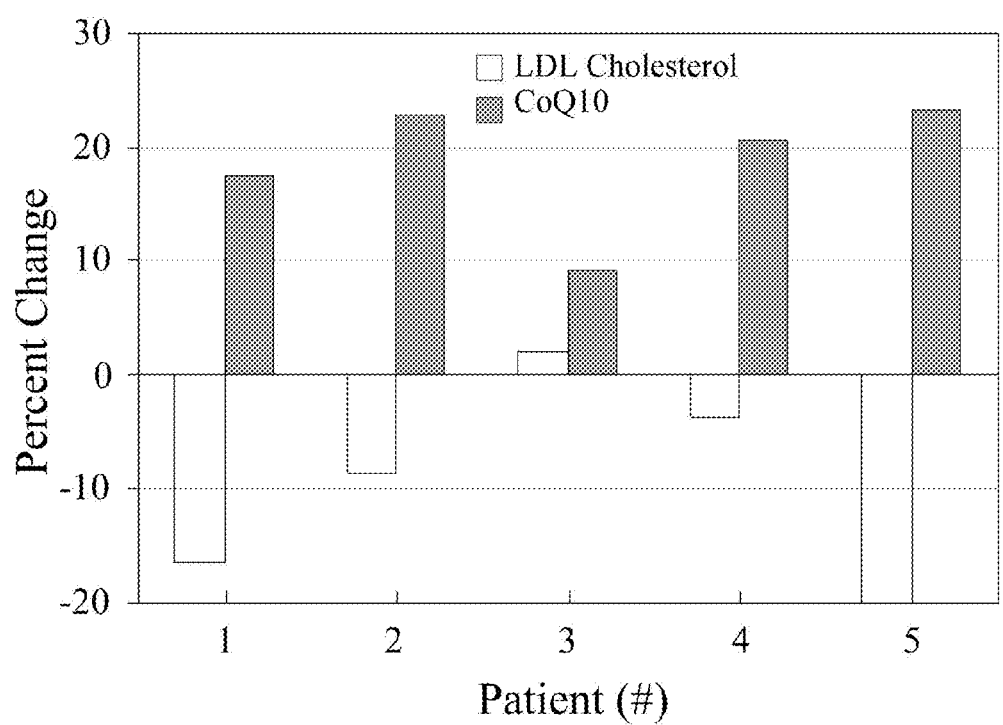
FIG. 3 illustrates the effect of annatto extract compositions on LDL and CoQ10.
Figure 4:
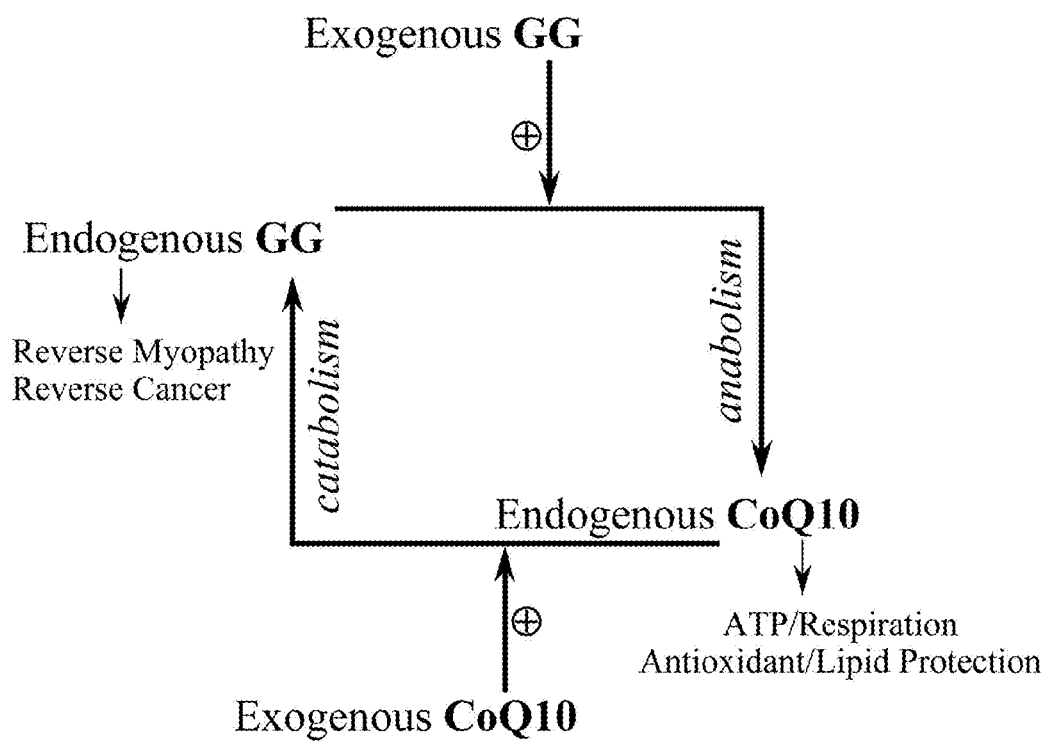
FIG. 4 illustrates the endogenous metabolism of CoQ10 and GG via respective exogenous GG and CoQ10.

Table 1 and FIG. 3 show the results of a study where the subjects took 20 mg/day of GG. According to the analytical method described in earlier section for anabolic conversion of GG to CoQ10, this is equivalent to the a theoretical conversion maximum of 30 mg/day (20×150/100) of CoQ10. Likewise, the 27 mg of GG/day consumed by the previous subject is equivalent to taking 40 mg CoQ10/day. Supplementation of GG for anabolic CoQ10 synthesis and supplementation CoQ10 for catabolic GG synthesis are reversible pathways and they are illustrated in FIG. 4.

Exogenously supplied GG raises the plasma CoQ10 to similar levels achieved by exogenous CoQ10, and the increase in plasma levels of 20 to 70% are illustrative. Higher doses of GG will cause the plasma CoQ10 to rise further to levels typically reached by humans (i.e., 2 to 5 folds above baseline levels) who take 30-1000 mg CoQ10/day, or more typically 100-300 mg CoQ10/day. High exogenous doses of CoQ10 is often required to achieve therapeutic plasma levels since supplemental CoQ10 has attendant problems with bioavailability in that less than 5% is absorbed. Supplementation of CoQ10 raises the gut-to-blood CoQ10 level while supplementation of AEC causes cell-to-blood rise of CoQ10. This represents the first reported endogenously available CoQ10 from GG and from AEC containing GG.

Example 3

Hypercholesterolemia

In borderline overweight volunteers (Table 2) on AEC, the T3-affected LDL drop corresponded with an increase in CoQ10 (Table 1 and FIG. 3). AEC treats hypercholesterolemia without decreasing CoQ10. In fact, the CoQ10 level rises (20%) when supplemented with AEC, affording additional antioxidant protection to LDL particles by CoQ10.

TABLE 2

Vital Statistics of Subjects

| Subject | Height (ft. in.) | Weight (lb) | Age | BMI (kg/m$^2$) |
|---|---|---|---|---|
| 1 | 5' 6" | 156 | 26 | 25.2 |
| 2 | 6' 1" | 190 | 22 | 25.1 |
| 3 | 5" 7" | 143 | 50 | 22.4 |
| 4 | 6' 2" | 204 | 30 | 26.3 |
| 5 | 5" 6" | 156 | 26 | 26.7 |

Administration of AEC prevents statin toxicities, increases CoQ10, protects the LDL, lowers cholesterol and improves endothelial functions.

Example 4

Cancer

GG is given as a drug adjunct for cancer therapy in general and for FTI therapy in particular.

Supplementation with GG in AEC reverses myotoxicities. GG is not toxic to untransformed cells or to normal cells and is used as a statin adjunct in cancer therapy.

CoQ10 catabolizes to GG and other smaller molecular weight substrates, which in turn inhibit the F— prenylated proteins.

GG is used alone or in conjunction with CoQ10 to provide ex vivo and in vivo GG substrate for prostate and breast cancer treatment.

AEC containing GG inhibits cancer growth where regardless of involvement of protein prenylation.

Example 5

Renal Insufficiency

GG and AEC are used in general and as an adjunct to the drugs used by kidney dialysis and renal insufficient patients.

Example 6

Organ Transplant

GG and AEC are used to reverse and/or minimize the serious myopathy and rhabdomyolysis of graft recipients, where GG and AEC are used as adjunct therapy to calcineurin inhibitors (cyclosporine in particular) and statins.

Example 7

Myotoxicities

Administration of GG reverses the side effect of drugs with a "common mechanism" of GG-depletion that causes a reduction of protein prenylation, which leads to myotoxicity.

Supplementation with AEC abrogates the effects of insufficient CYP3A4 processing of statin (in mono- or combo-therapies) and reverses the compromise on the vascular system.

Also, GG and AEC is used as an adjunct to mono- and combo-therapies including fibrates, and in particular, in treatment regimens used in patients with prediabetes and diabetes, and hypertriglyceridemia.

Example 8

PPAR Activation

Unexpectedly the triglyceride (TG) dropped (20-30%) in the first 3 months for patients on GG and AEC. Table 3 compares the data of lipid management of normal weight and overweight/obese subjects. The cholesterol management (i.e., TC and LDL) improved in both groups and the TG dropped again in both groups. The HDL in overweight and normal subjects rose by 4% and 10%, respectively. Though modest, the HDL increased with AEC supplementation. It was clearly documented that AEC effectively treated lipidemia of normal weight and overweight/obese subjects, and particularly the TG dropped.

TABLE 3

Supplementation of AEC on normal weight and overweight/obese lipidemic subjects*.

| Subjects | TC (↓) | LDL (↓) | TG (↓) | HDL (↑) |
|---|---|---|---|---|
| Normal Weight | 13% | 15% | 21% | 10% |
| Overweight/Obese | 15% | 10% | 20% | 4% |

*Subjects are moderately hypercholesterolemic (ca 250 mg/dl). Each group has 5 subjects.

GG behaved like a TZD as GG metabolic effects matched for TZD. Also, GG behaved like a fibrate because of the disposal of TG from circulation. Put together, AEC containing GG activates the nuclear transcription factor PPAR (γ, α, δ or mixed) and thereby carried out the metabolic effects similar to those of TZDs and fibrates, in various tissues of common sites (adipose, skeletal muscle, and kidney, macrophage, VSMC, endothelial cell) and in various tissues of different sites for PPARγ (heart, gut) and PPARα (liver). These various PPAR expressions shared more common sites than different ones. Mixed PPAR activation, besides PPARγ and PPARα, also included PPARδ whose expression was ubiquitous in all tissues.

Example 9

Insulin Resistance

The IR criteria were assessed on humans supplemented with AEC containing GG (Table 4). Both TG/HDL and TG dropped approximately 20-30% in normal weight subjects (2-month and 3-month studies) and in overweight subjects (8-month study). Unexpectedly, the AEC containing GG improved insulin sensitivity (IS) as evaluated by the two surrogate markers. Additionally, based on the TG/HDL ratios, 50% of the subjects in all groups (Table 4) reversed back to IS from previously being IR prior to supplementation.

TABLE 4

Improvement and reversal of insulin resistance (IR) in subjects on AEC*

| Surrogate Marker | 2-month study (normal weight) | 3-month study (normal weight) | 8-month study (overweight) |
|---|---|---|---|
| TG | 21.2% ↓ (1 in 5)@ | 27.9% ↓ (1 in 2) | 19.6% ↓ (2 in 5) |
| TG/HDL | 27.7% ↓ (2 in 4) | 28.0% ↓ (1 in 2) | 21.2% ↓ (1 in 2) |

*Each study group has 5 subjects. Typically 4 of 5 subjects in each group have improved TG and TG/HDL showing improved insulin sensitivity.
@Using two IR surrogate markers (criteria; TG ≧ 140 mg/dl and/or TG/HDL ≧ 3.5), the number of subjects that reversed back to insulin sensitivity that were IR prior to AEC supplementation.

One subject had a 43% drop in TG (from 121 mg/dL before supplementation to 69 mg/dL 16 months after AEC supplementation). Correspondingly, the TG/HDL ratios dropped 35% (from 1.86 before supplementation to 1.21 at 16 months after AEC supplementation). Therefore, improvement in insulin action and reversal of IR was not transient (Tables 4 and 5). The study duration was meant to be illustrative for managing IR where effectiveness is seen in just one month of supplementation, and lasts indefinitely with continued usage. Taken together, the AEC containing GG potentiated IS and reversed IR in the various study durations, in normal weight and overweight/obese subjects, and in both sexes. Furthermore, such insulin potentiation and IR reversal by GG reduced the risk of CVD, T2DM, hypertension, PCOS and alcohol-unrelated fatty liver disease.

GG reversed statin-induced IR by reviving Glut 4 synthesis. Taken together, AEC in general, and GG in particular lowered triglyceride, improved IS and reversed IR. AEC containing GG activated mixed PPARs and potentiated Glut 4 and thereby reversed and/or reduced the severity of metabolic syndrome. Application of AEC reverses IR by salvaging the GG-prenylation of Glut 4 and is related to TG drop (Table 5).

TABLE 5

Effect of annatto extract supplementation on blood triglyceride.*

| | Blood TG level (mg/dL) | | |
|---|---|---|---|
| Subject | Control | After | Change (%) |
| 1 | 228 | 203 | −11.0 |
| 2 | 92 | 100 | 8.7 |
| 3 | 164 | 96 | −41.5 |
| 4 | 180 | 176 | −2.2 |
| 5 | 276 | 205 | −25.7 |
| Mean | 188 | 156 | −17.0 |

*Subjects took Annatto extract composition (3 softgels/day containing a total of 20 mg GG and 75 mg T3) for 2 months.

Example 10

Sterol Regulatory Element Binding Protein-1

The studies showed that AEC containing GG reduced IR, and lipids (Tables 4 and 5) where TG consistently dropped. Therefore, AEC containing GG in general, and the GG in particular, deactivated the transcription factor SREBP-1 expression, and thereby inhibited the de novo synthesis of fatty acid and TG in various organs, including liver, adipose and skeletal muscle. Administration of AEC containing GG simultaneously deactivates SREBP-1 and activates PPAR, which controls FFA/TG regulation in concert in both the metabolism (anabolism and catabolism) and synthesis.

Example 11

Other Uses

GG is used as an adjunctive when a patient is on medication (e.g. statin, bisphosphonate, cyclosporine, fibrate, FTI, niacin, warfarin/coumadin, antifungal, and antibiotic) or any combination of medications thereof.

GG is used to prevent "pill esophagitis" where GG is an excipient in the film-coat of compressed tablets, softgel gelatin, hard gel two-piece gelatin, beads, granules, and liquid coats.

GG is used as a preventative to promote general upper GI health.

GG is administrated to patients who are on combined corticosteroid and bisphosphonate medications.

GG is used to promote general skin health and healing via prenylation of epithelial cells.

GG is used to prevent drug-induced cataract formation. An unique application of AEC containing GG is to mix it with tocotrienols, including AEC containing tocotrienols, to attain simultaneous benefits of cataract inhibition by GG and cholesterol inhibition by tocotrienols in the eyes. This application is ordinarily consumed as GG and T3 in a softgel form. Alternatively, these two lipid compounds are emulsified into a liquid for used as an eye drop. To those skilled in the art, other ocularly beneficial compounds can be added, including lutein, ascorbic acid and zinc.

Example 12

Formulation with GG

GG and AEC are formulated with other synergistic and useful non-drug vitamin nutrients. GG is formulated with niacin (to manage lipids) and with other B Vitamins (as they are needed for energy supply and CoQ10 synthesis). GG and AEC may be added to ubiquinone (exogenous CoQ10 supply), idebenone (mitochondrial respiration support), omega-3s (to lower triglyceride), and linseed/flaxseed oil (to improve GG levels). GG and AEC are added to plaunotol and to other GI track support nutrients (where GG supports the upper GI track and other nutrients support the lower GI track) to provide support for the entire "upper-lower" alimentary canal. GG and AEC are mixed with tocotrienols and tocotrienol rich fractions (e.g., from palm and rice sources) to promote nerve health, particularly the autonomal nervous system and to improve immune health. GG and AEC are added to other non-vitamin endogenous nutrients, which include but not limited to, carnitines, CoQ10, alpha lipoic acid, omega 3 fatty acids, creatine, SOD, and NADH. GG, an endogenous nutrient, is thereby formulated with other endogenous nutrients.

GG and AEC is formulated with other drugs, especially to lessen or eliminate their toxicities. Specific examples included, but not limited to, are statins, bisphosphonates, fibrates, cyclosporines, niacin, warfarin/coumadin, antifungals, and antibiotics.

What is claimed is:

1. A medicament consisting essentially of:
an annatto extract of geranyl geraniol; and
a litchi seed extract of tocochromanol.

2. A medicament consisting essentially of:
an annatto extract of geranyl geraniol;
a litchi seed extract of tocochromanol; and
at least one non-vitamin nutrient selected from the group consisting of ubiquinone, idebenone, plaunotol, carnitine, CoQ10, alpha lipoic acid, omega 3 fatty acid, creatine, superoxide dismutase (SOD), and nicotinamide adenine dinucleotide (NADH).

3. A medicament consisting essentially of:
an annatto extract of geranyl geraniol;
a litchi seed extract of tocochromanol;
at least one non-vitamin nutrient selected from the group consisting of ubiquinone, idebenone, plaunotol, carnitine, CoQ10, alpha lipoic acid, omega 3 fatty acid, creatine, superoxide dismutase (SOD), and nicotinamide adenine dinucleotide (NADH); and
at least one drug selected from the group consisting of statin, bisphosphonate, fibrate, cyclosporine, niacin, vitamin B, warfarin, and coumadin.

4. A medicament consisting essentially of:
an annatto extract of geranyl geraniol;
a litchi seed extract of tocochromanol; and
at least one drug selected from the group consisting of statin, bisphosphonate, fibrate, cyclosporine, niacin, vitamin B, warfarin, and coumadin.

5. The medicament of claim 1, wherein the tocochromanol has a delta-to-gamma ratio of tocotrienol between 1:100 and 100:1.

6. The medicament of claim 2, wherein the tocochromanol has a delta-to-gamma ratio of tocotrienol between 1:100 and 100:1.

7. The medicament of claim 3, wherein the tocochromanol has a delta-to-gamma ratio of tocotrienol between 1:100 and 100:1.

8. The medicament of claim 4, wherein the tocochromanol has a delta-to-gamma ratio of tocotrienol between 1:100 and 100:1.

* * * * *